(12) United States Patent
Donlon et al.

(10) Patent No.: US 11,026,759 B2
(45) Date of Patent: *Jun. 8, 2021

(54) SPLAYED CABLE GUIDE FOR A MEDICAL INSTRUMENT

(71) Applicant: Intuitive Surgical Operations, Inc., Sunnyvale, CA (US)

(72) Inventors: Edward P. Donlon, San Jose, CA (US); Craig Tsuji, San Jose, CA (US); Alain Sadaka, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/810,429

(22) Filed: Mar. 5, 2020

(65) Prior Publication Data

US 2020/0197117 A1 Jun. 25, 2020

Related U.S. Application Data

(63) Continuation of application No. 16/453,530, filed on Jun. 26, 2019, now Pat. No. 10,595,949, which is a
(Continued)

(51) Int. Cl.
*F16C 1/10* (2006.01)
*A61B 17/32* (2006.01)
(Continued)

(52) U.S. Cl.
CPC ...... *A61B 34/71* (2016.02); *A61B 17/320016* (2013.01); *A61B 34/35* (2016.02);
(Continued)

(58) Field of Classification Search
CPC ........ A61B 17/320016; A61B 18/1445; A61B 34/35; A61B 34/71; A61B 2017/00477;
(Continued)

(56) References Cited

U.S. PATENT DOCUMENTS 793,510 A 6/1905 Cramer et al.
2,186,181 A 1/1940 Gustav et al.
(Continued)

FOREIGN PATENT DOCUMENTS

CN 104116547 A 10/2014
EP 2362285 A2 8/2011
(Continued)

OTHER PUBLICATIONS

Office Action for U.S. Appl. No. 16/453,530, dated Aug. 30, 2019.
(Continued)

*Primary Examiner* — Adam D Rogers

(57) ABSTRACT

An apparatus includes a housing, a cable guide, a first cable, and a second cable. The housing is coupled to a shaft of a medical instrument. The cable guide is coupled to the housing, and defines a shaft opening into a passageway defined by the shaft. A first guide groove and a second guide groove are defined by the cable guide, with each of the first guide groove and the second guide groove being splayed outward from the shaft opening. The first cable is routed within the first guide groove and through the shaft opening, and is configured to slide within the first guide groove. The second cable is routed within the second guide groove and through the shaft opening, and is configured to slide within the second guide groove.

20 Claims, 20 Drawing Sheets

Related U.S. Application Data continuation of application No. 15/903,139, filed on Feb. 23, 2018, now Pat. No. 10,357,321.

(60) Provisional application No. 62/463,105, filed on Feb. 24, 2017.

(51) Int. Cl.
*A61B 34/00* (2016.01)
*A61B 34/35* (2016.01)
*A61B 18/14* (2006.01)
*A61B 17/00* (2006.01)

(52) U.S. Cl.
CPC .......... *F16C 1/106* (2013.01); *A61B 18/1445* (2013.01); *A61B 2017/00477* (2013.01)

(58) Field of Classification Search
CPC ...... A61B 2034/305; F16C 1/10; F16C 1/103; F16C 1/105; F16C 1/106; F16C 1/18; F16C 1/26
See application file for complete search history.

(56) References Cited

U.S. PATENT DOCUMENTS

| | | | |
|---|---|---|---|
| 3,618,420 | A | 11/1971 | Horwitt et al. |
| 4,341,144 | A | 7/1982 | Milne |
| 4,899,608 | A | 2/1990 | Knappe et al. |
| 5,792,135 | A | 8/1998 | Madhani et al. |
| 5,807,377 | A | 9/1998 | Madhani et al. |
| 5,876,325 | A | 3/1999 | Mizuno et al. |
| 6,007,550 | A | 12/1999 | Wang et al. |
| 6,331,181 | B1 | 12/2001 | Tierney et al. |
| 6,371,952 | B1 | 4/2002 | Madhani et al. |
| 6,394,998 | B1 | 5/2002 | Wallace et al. |
| 6,676,684 | B1 | 1/2004 | Morley et al. |
| 6,817,974 | B2 | 11/2004 | Cooper et al. |
| 6,994,708 | B2 | 2/2006 | Manzo et al. |
| 7,048,745 | B2 | 5/2006 | Tierney et al. |
| 7,090,683 | B2 | 8/2006 | Brock et al. |
| 7,169,141 | B2 | 1/2007 | Brock et al. |
| 7,214,230 | B2 | 5/2007 | Brock et al. |
| 7,331,967 | B2 | 2/2008 | Lee et al. |
| 7,371,210 | B2 | 5/2008 | Brock et al. |
| 7,524,320 | B2 | 4/2009 | Tierney et al. |
| 7,582,055 | B2 | 9/2009 | Komiya et al. |
| 7,608,056 | B2 | 10/2009 | Kennedy, II et al. |
| 7,608,083 | B2 | 10/2009 | Lee et al. |
| 7,666,191 | B2 | 2/2010 | Orban, III et al. |
| 7,935,130 | B2 | 5/2011 | Williams |
| 8,444,631 | B2 | 5/2013 | Yeung et al. |
| 8,479,969 | B2 | 7/2013 | Shelton, IV et al. |
| 8,506,555 | B2 | 8/2013 | Ruiz et al. |
| 8,551,115 | B2 | 10/2013 | Steger et al. |
| 8,597,280 | B2 | 12/2013 | Cooper et al. |
| 8,771,270 | B2 | 7/2014 | Burbank et al. |
| 8,800,838 | B2 | 8/2014 | Shelton, IV et al. |
| 8,808,166 | B2 | 8/2014 | Hosaka |
| 8,911,471 | B2 | 12/2014 | Spivey et al. |
| 8,992,565 | B2 | 3/2015 | Brisson et al. |
| 9,028,494 | B2 | 5/2015 | Shelton, IV et al. |
| 9,078,684 | B2 | 7/2015 | Williams et al. |
| 9,204,923 | B2 | 12/2015 | Manzo et al. |
| 9,232,979 | B2 | 1/2016 | Parihar et al. |
| 9,259,274 | B2 | 2/2016 | Prisco |
| 9,839,439 | B2 | 12/2017 | Cooper et al. |
| 9,931,106 | B2 | 4/2018 | Au et al. |
| 9,962,066 | B2 | 5/2018 | Rogers et al. |
| 9,962,228 | B2 | 5/2018 | Schuh et al. |
| 10,130,366 | B2 | 11/2018 | Shelton, IV et al. |
| 10,219,874 | B2 | 3/2019 | Yu et al. |
| 10,357,321 | B2 | 7/2019 | Donlon et al. |
| 10,550,918 | B2 | 2/2020 | Cooper et al. |
| 10,595,949 | B2 | 3/2020 | Donlon et al. |
| 10,682,141 | B2 | 6/2020 | Moore et al. |
| 10,779,898 | B2 | 9/2020 | Hill et al. |
| 2002/0111635 | A1 | 8/2002 | Jensen et al. |
| 2005/0119527 | A1 | 6/2005 | Banik et al. |
| 2006/0074415 | A1 | 4/2006 | Scott et al. |
| 2007/0119274 | A1 | 5/2007 | Devengenzo et al. |
| 2007/0137371 | A1 | 6/2007 | Devengenzo et al. |
| 2007/0232858 | A1 | 10/2007 | MacNamara et al. |
| 2008/0009838 | A1 | 1/2008 | Schena et al. |
| 2008/0046122 | A1 | 2/2008 | Manzo et al. |
| 2008/0065102 | A1 | 3/2008 | Cooper |
| 2008/0065105 | A1 | 3/2008 | Larkin et al. |
| 2008/0087871 | A1 | 4/2008 | Schena et al. |
| 2008/0103491 | A1 | 5/2008 | Omori et al. |
| 2008/0196533 | A1 | 8/2008 | Bergamasco et al. |
| 2009/0088774 | A1 | 4/2009 | Swarup et al. |
| 2009/0198272 | A1 | 8/2009 | Kerver et al. |
| 2010/0011900 | A1 | 1/2010 | Burbank et al. |
| 2010/0170519 | A1 | 7/2010 | Romo et al. |
| 2010/0175701 | A1 | 7/2010 | Reis et al. |
| 2010/0198253 | A1 | 8/2010 | Jinno et al. |
| 2010/0318101 | A1 | 12/2010 | Choi et al. |
| 2011/0015650 | A1 | 1/2011 | Choi et al. |
| 2011/0118754 | A1 | 5/2011 | Dachs, II et al. |
| 2011/0277580 | A1 | 11/2011 | Cooper et al. |
| 2011/0277775 | A1 | 11/2011 | Holop et al. |
| 2011/0295269 | A1 | 12/2011 | Swensgard et al. |
| 2011/0295270 | A1 | 12/2011 | Giordano et al. |
| 2012/0046522 | A1 | 2/2012 | Naito |
| 2012/0123441 | A1 | 5/2012 | Au et al. |
| 2012/0239060 | A1 | 9/2012 | Orban, III et al. |
| 2012/0289974 | A1 | 11/2012 | Rogers et al. |
| 2012/0298719 | A1 | 11/2012 | Shelton, IV et al. |
| 2013/0046318 | A1 | 2/2013 | Radgowski et al. |
| 2013/0144395 | A1 | 6/2013 | Stefanchik et al. |
| 2014/0005678 | A1 | 1/2014 | Shelton, IV et al. |
| 2014/0114327 | A1 | 4/2014 | Boudreaux et al. |
| 2014/0257333 | A1 | 9/2014 | Blumenkranz |
| 2015/0150635 | A1 | 6/2015 | Kilroy et al. |
| 2015/0150636 | A1 | 6/2015 | Hagn et al. |
| 2015/0157355 | A1 | 6/2015 | Price et al. |
| 2016/0184034 | A1 | 6/2016 | Holop et al. |
| 2016/0184036 | A1 | 6/2016 | Solomon et al. |
| 2016/0361049 | A1 | 12/2016 | Dachs, II et al. |
| 2017/0007345 | A1 | 1/2017 | Smith et al. |
| 2017/0165017 | A1 | 6/2017 | Chaplin et al. |
| 2018/0126546 | A1 | 5/2018 | Vaders |
| 2019/0125468 | A1* | 5/2019 | Adams .................. A61B 34/35 |
| 2019/0231464 | A1 | 8/2019 | Wixey et al. |
| 2019/0307522 | A1 | 10/2019 | Lambrecht et al. |
| 2019/0328467 | A1 | 10/2019 | Waterbury et al. |

FOREIGN PATENT DOCUMENTS

| | | |
|---|---|---|
| EP | 2548529 A1 | 1/2013 |
| EP | 2783643 A1 | 10/2014 |
| EP | 3195993 A1 | 7/2017 |
| JP | H06114000 A | 4/1994 |
| JP | H10249777 A | 9/1998 |
| JP | 2002200091 A | 7/2002 |
| JP | 2005288590 A | 10/2005 |
| WO | WO-9729690 A1 | 8/1997 |
| WO | WO-2010081050 A1 | 7/2010 |
| WO | WO-2013118774 A1 | 8/2013 |
| WO | WO-2015142290 A1 | 9/2015 |
| WO | WO-2016161449 A1 | 10/2016 |
| WO | WO-2016172299 A1 | 10/2016 |
| WO | WO-2018013313 A1 | 1/2018 |
| WO | WO2018/049217 A1 | 3/2018 |
| WO | WO-2018069679 A1 | 4/2018 |
| WO | WO-2018094191 A1 | 5/2018 |
| WO | WO2020/102776 A1 | 5/2020 |
| WO | WO2020/252184 A1 | 12/2020 |

OTHER PUBLICATIONS

Office Action dated Nov. 21, 2018 for U.S. Appl. No. 15/903,139, filed Feb. 23, 2018, 10 pages.

(56) References Cited

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for EP 17828154.9, dated Jun. 24, 2020, 11 pages.

* cited by examiner

SPLAYED CABLE GUIDE FOR A MEDICAL INSTRUMENT

CROSS-REFERENCE TO RELATED APPLICATIONS

This application is a continuation of U.S. patent application Ser. No. 16/453,530 (filed Jun. 26, 2019), entitled "Splayed Cable Guide for a Medical Instrument," which is a continuation of U.S. patent application Ser. No. 15/903,139 (filed Feb. 23, 2018), now U.S. Pat. No. 10,357,321, entitled "Splayed Cable Guide for a Medical Instrument," which claims benefit of priority to U.S. Provisional Patent Application No. 62/463,105 (filed Feb. 24, 2017), entitled "Splayed Cable Guide," each of which is incorporated herein by reference in its entirety.

BACKGROUND

The embodiments described herein relate to mechanisms for routing cables, more specifically to medical devices, and still more specifically to endoscopic tools. More particularly, the embodiments described herein relate control cable routing in surgical instruments for teleoperated medical devices.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of an extension (also referred to herein as the main tube or shaft). The wrist mechanism may provide one or more orientation, translation, or combinations of orientation and translation degrees of freedom for the end effector. The end effector often has one or more additional mechanical degrees of freedom, such as a scissors or grip degree of freedom. In some instances, the wrist and end effector degrees of freedom may be combined in a single mechanism, such as a combined yaw and grip degree of freedom.

To enable the desired movement of the wrist mechanism and end effector, known instruments include tension members (e.g., cables, tension bands) that extend through the main tube of the instrument and that connect the wrist mechanism to a transmission or actuator (also referred to herein as a backend mechanism). The backend mechanism moves the cables to operate the wrist mechanism. For robotic or teleoperated systems, the backend mechanism is motor driven and can provide mechanical force or torque input to the backend, and this force or torque is transmitted to one or more cables in order to operate the wrist or end effector degrees of freedom.

Known backend systems employ one or more pulleys to route the control cables from the backend mechanism and into the shaft. Although known arrangements reduce friction associated with cable movement and bends, the use of pulleys and shafts increases cost, complexity, and assembly time. Thus, a need exists for mechanism for routing tension members between the proximal end (i.e., the backend mechanism) and the distal end (i.e., the wrist mechanism) of medical instruments. A need also exists for improved cable routing mechanisms having reduced size, reduced part count, lower cost of materials, and which permit easy assembly including installation of tension members.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, an apparatus includes a housing, a cable guide, a first cable, and a second cable. The housing is coupled to a shaft of a medical instrument. The cable guide is coupled to the housing and defines a shaft opening into a passageway defined by the shaft. A first guide groove and a second guide groove are defined by the cable guide, with each of the first guide groove and the second guide groove being splayed outward from the shaft opening. The first cable is routed within the first guide groove and through the shaft opening, and is configured to slide within the first guide groove. The second cable is routed within the second guide groove and through the shaft opening and is configured to slide within the second guide groove.

In some embodiments, an apparatus includes a housing, a cable guide, a first cable, and a second cable. The housing is coupled to a shaft of a medical instrument. The cable guide is coupled to the housing and defines a shaft opening into a passageway defined by the shaft. The cable guide includes a first guide surface and a second guide surface. A first guide groove is defined by the first guide surface, which includes a first bend portion transitioning from the first guide groove to the shaft opening. The first bend portion is characterized by a first bend radius about a first bend axis. A second guide groove is defined by the second guide surface, which includes a second bend portion transitioning from the second guide groove to the shaft opening. The second bend portion is characterized by a second bend radius about a second bend axis. The second bend axis is nonparallel to the first bend axis. The first cable is routed within the first guide groove and through the shaft opening. The second cable is routed within the second guide groove and through the shaft opening.

DETAILED DESCRIPTION

Figure 1:
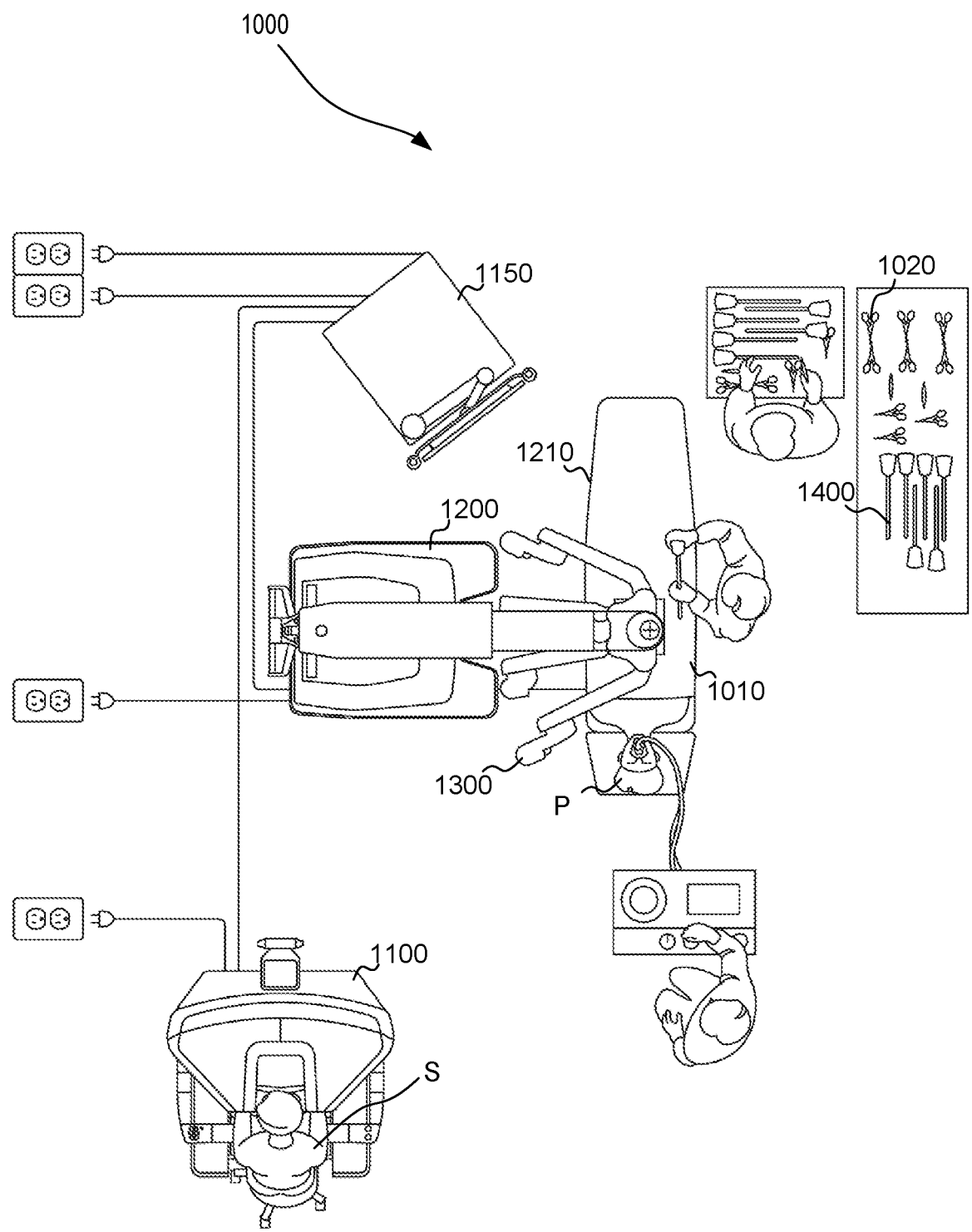
FIG. 1 is a plan view of a minimally invasive teleoperated medical system according to an embodiment, being used to perform a medical procedure such as surgery.

The embodiments described herein can advantageously be used in a wide variety of grasping, cutting, and manipulating operations associated with minimally invasive surgery. As described herein, the instruments include one or more cables (which act as tension members) that can be moved to actuate the end effector with multiple degrees of freedom. Moreover, the cables can be routed via one or more cable guides of types shown and described herein.

In some embodiments, an apparatus includes a housing, a cable guide, a first cable, and a second cable. The housing is coupled to a shaft of a medical instrument. The cable guide is coupled to the housing and defines a shaft opening into a passageway defined by the shaft. A first guide groove and a second guide groove are defined by the cable guide, with each of the first guide groove and the second guide groove being splayed outward from the shaft opening. The first cable is routed within the first guide groove and through the shaft opening, and the first cable is configured to slide within the first guide groove. The second cable is routed within the second guide groove and through the shaft opening, and the second cable is configured to slide within the second guide groove.

In some embodiments, an apparatus includes a housing, a cable guide, a first cable, and a second cable. The housing is coupled to a shaft of a medical instrument. The cable guide is coupled to the housing and defines a shaft opening into a passageway defined by the shaft. A first guide groove and a second guide groove are defined by the housing. A first centerline of the first guide groove is nonparallel to a second centerline of the second guide groove. The first cable is routed within the first guide groove and through the shaft opening, and the first cable is configured to slide within the first guide groove. The second cable is routed within the second guide groove and through the shaft opening, and the second cable is configured to slide within the second guide groove.

In some embodiments, an apparatus includes a housing, a cable guide, a first cable, and a second cable. The housing is coupled to a shaft of a medical instrument. The cable guide is coupled to the housing and defines a shaft opening into a passageway defined by the shaft. The cable guide includes a first guide surface and a second guide surface. A first guide groove is defined by the first guide surface, which includes a first bend portion transitioning from the first guide groove to the shaft opening. The first bend portion is characterized by a first bend radius about a first bend axis. A second guide groove is defined by the second guide surface, which includes a second bend portion transitioning from the second guide groove to the shaft opening. The second bend portion is characterized by a second bend radius about a second bend axis. The second bend axis is nonparallel to the first bend axis. The first cable is routed within the first guide groove and through the shaft opening. The second cable is routed within the second guide groove and through the shaft opening.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, Calif. Examples of such surgical systems are the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled tool assembly 1400 (also referred to herein as a "tool") through a minimally invasive incision in the body or natural orifice of the patient P while the surgeon S views the surgical site and controls movement of the tool 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of tools 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
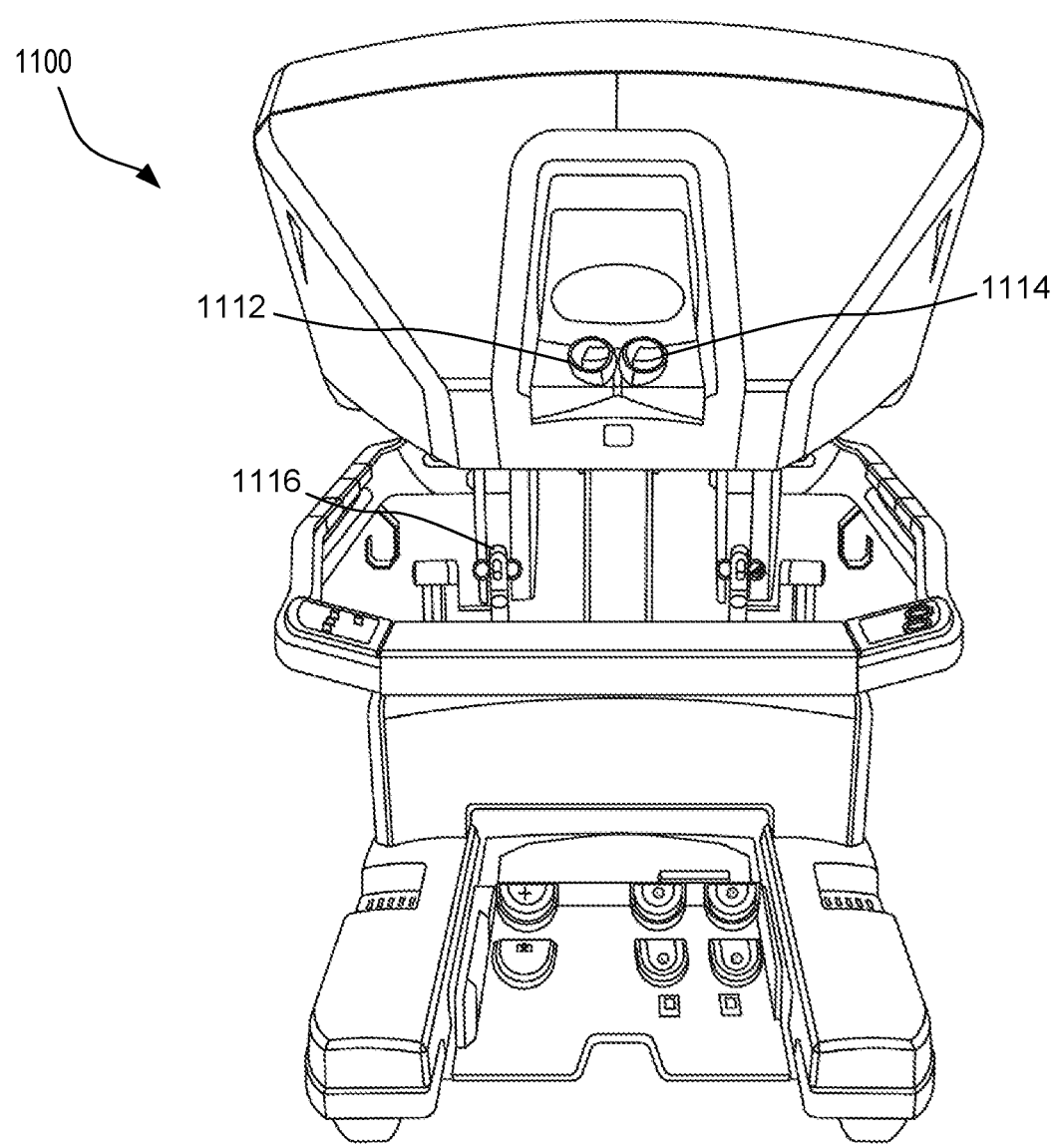
FIG. 2 is a perspective view of a user control unit of the minimally invasive teleoperated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments, however, the user control unit 1100 and the surgeon S can be in a different room, a completely different building, or other remote location from the patient allowing for remote surgical procedures.

Figure 3:
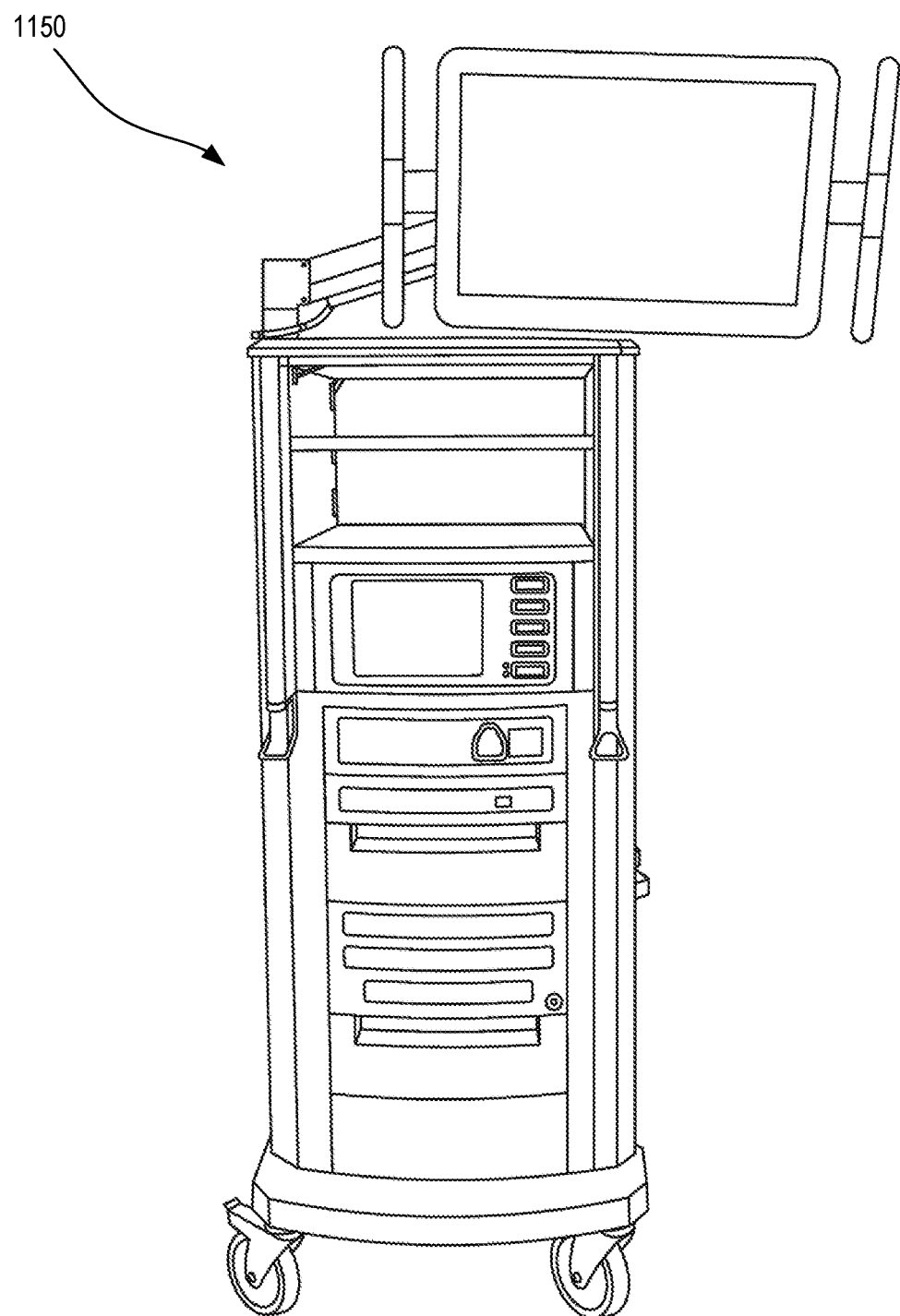
FIG. 3 is a perspective view of an optional auxiliary unit of the minimally invasive teleoperated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
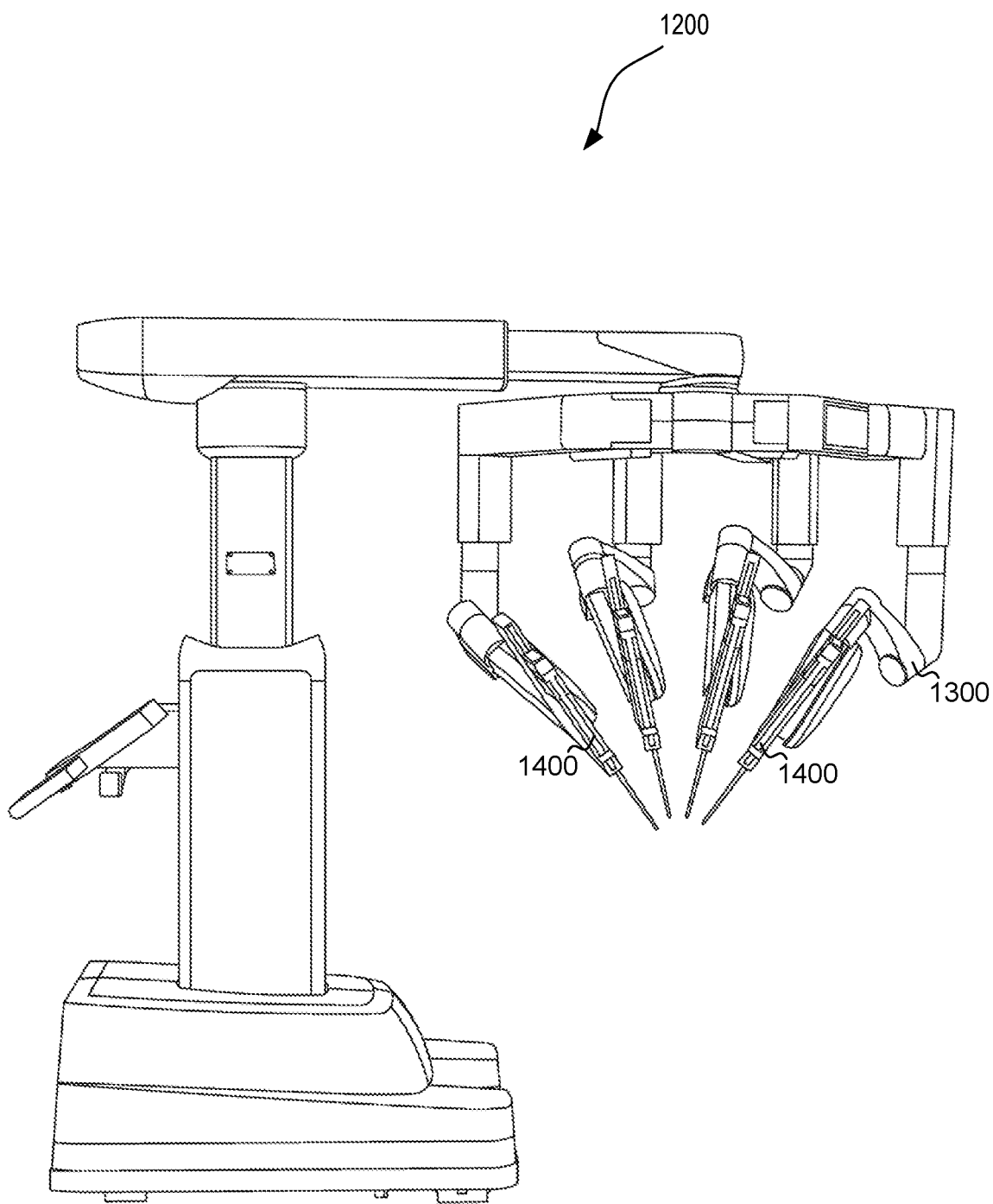
FIG. 4 is a front view of a manipulator unit, including a plurality of instruments, of the minimally invasive teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a kinematic remote center of motion is maintained at the incision or orifice. In this manner, the incision size can be minimized.

Figure 5:
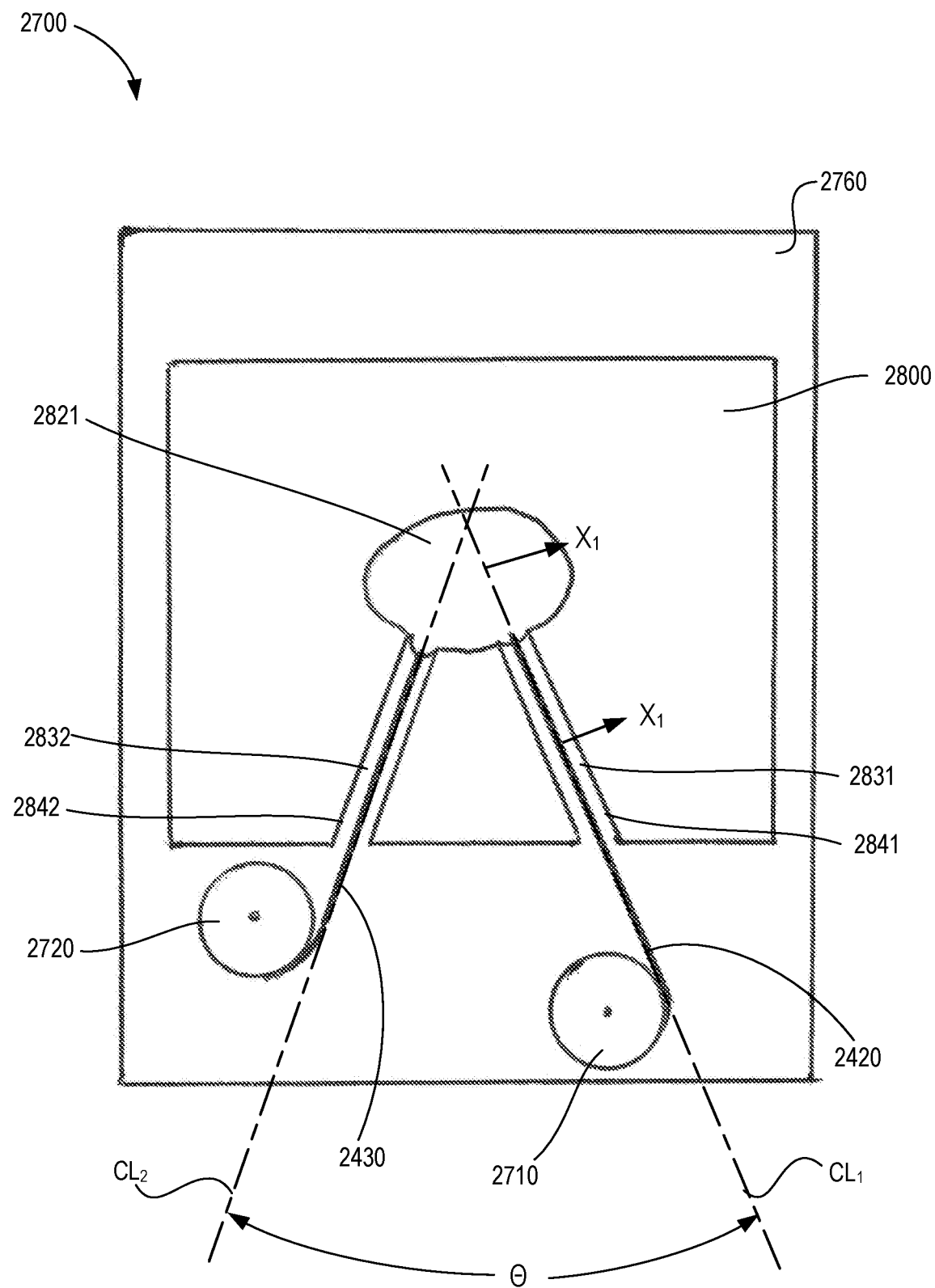
FIG. 5 is a diagrammatic top view of a portion of an instrument of a surgery system in a first position, according to an embodiment.
Figure 6:
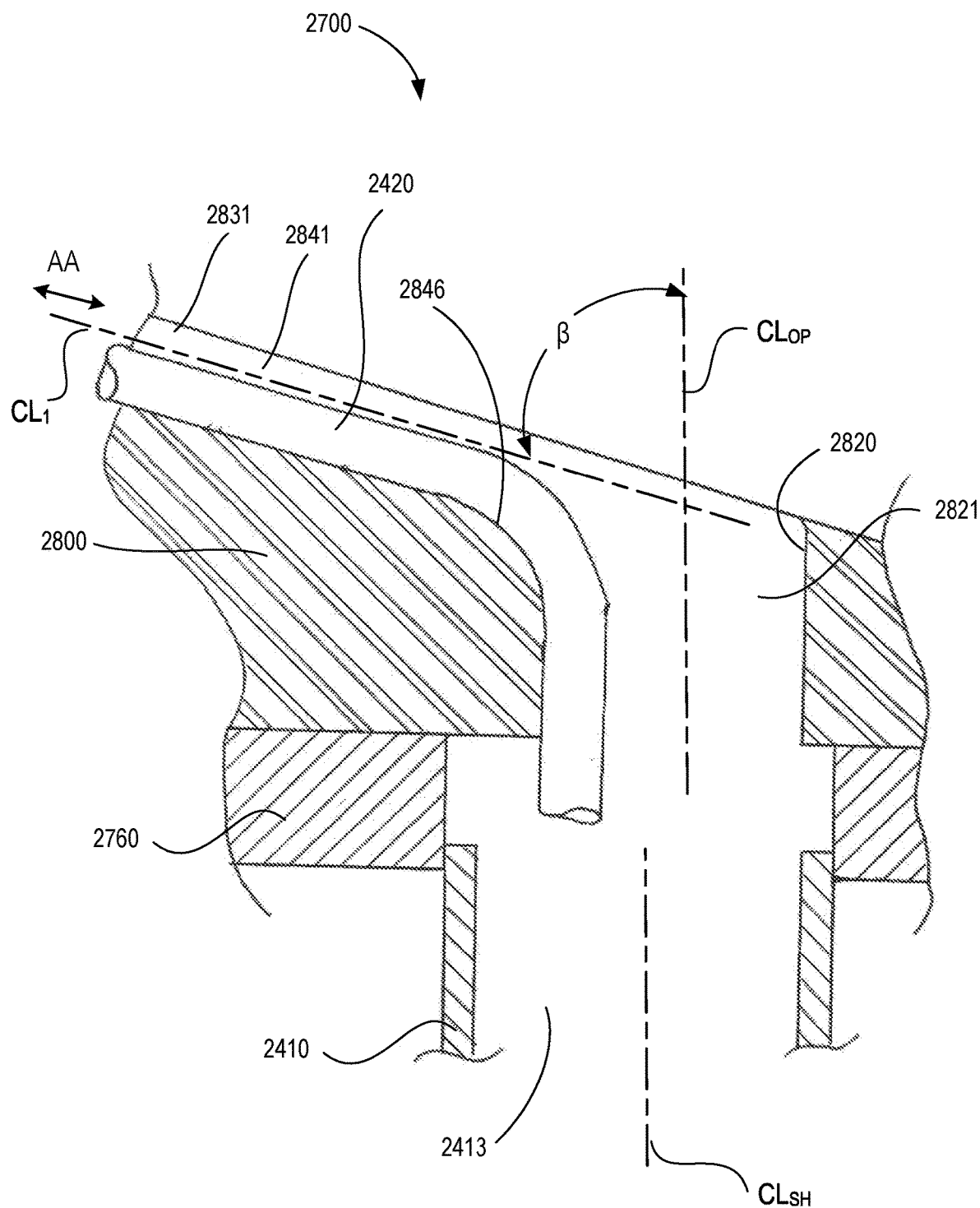
FIG. 6 is a diagrammatic side view of the portion of the instrument shown in FIG. 5 taken along line $X_1$-$X_1$ in FIG. 5.

FIGS. 5 and 6 are diagrammatic illustrations of various portions of a transmission 2700, according to an embodiment. The transmission 2700 can be included in any of the instruments shown and described herein (e.g., the instrument 4400) and can function as an actuator to move one or more tensions members (e.g., the first cable 2420 and the second cable 2430) to actuate any suitable end effector. In some embodiments, the transmission 2700 or any of the components therein are optionally parts of a surgical system that performs minimally invasive surgical procedures and which can include a manipulator unit, a series of kinematic linkages, a series of cannulas, or the like. The transmission 2700 (and any of the instruments described herein) can be used in any suitable surgical system, such as the MIRS system 1000 shown and described above. The transmission 2700 includes a chassis 2760, a first actuator 2710, a second actuator 2720, and a cable guide 2800.

The chassis 2760 (which functions as a housing) provides the structural support for mounting and aligning the components of the transmission 2700. For example, as shown in FIG. 6, the chassis 2760 is coupled to a shaft 2410 of a medical instrument. The shaft 2410 can be any suitable elongated shaft that couples a wrist assembly, end effector, or other component (not shown) to the transmission 2700. Specifically, the shaft 2410 includes a proximal end portion that is coupled to the chassis 2760. The shaft 2410 defines at least one passageway 2413 through which the first cable 2420, the second cable 2430, and other components (e.g., energized electrical wires, ground wires, or the like, not shown in FIGS. 5 and 6) can be routed from the transmission 2700 towards a wrist assembly, end effector, or other component. Although shown as including a single passageway 2413 that defines a shaft center line $CL_{SH}$, in other embodiments, the shaft 2410 can define multiple passageways. Moreover, although the chassis 2760 is shown as defining an opening within which the proximal end portion of an instrument shaft 2410 is mounted, in other embodiments, the shaft 2410 can be coupled to the chassis 2760 by any suitable mechanism (e.g., a flange connection).

The chassis 2760 also provides support structure and mounting structure to which the first actuator 2710 and the second actuator 2720 are mounted. In addition to providing mounting support for the internal components of the transmission 2700, the chassis 2760 can also include external features (not shown, but which can be recesses, clips, etc.) that interface with a docking port of a drive device (not shown). The drive device can be, for example, a computer-assisted teleoperated surgical system that can receive the transmission 2700 and manipulate the transmission 2700 to perform various surgical operations. In other embodiments, the drive device can be an assembly system that can receive and manipulate the transmission 2700 to perform various assembly operations.

The first actuator 2710 is any suitable actuator that can apply a force to or move the first cable 2420 (see the arrow AA in FIG. 6 showing movement of the first cable 2420). Similarly, the second actuator 2720 is any suitable actuator that can apply a force to or move the second cable 2430. Movement of the first cable 2420 and the second cable 2430 within the transmission 2700 and through the shaft 2410 can produce the desired movement (e.g., rotating, gripping, etc.) of the wrist assembly, end effector, or other component coupled to the distal end portion of the shaft 2410. The first actuator 2710 and the second actuator 2720 can each be any suitable mechanism or assembly for applying a force to or moving the cables. For example, in some embodiments, the first actuator 2710, the second actuator 2720, or both can be a motor-driven rotating actuator (e.g., a capstan) that winds or unwinds a cable to cause the desired movement of the cable. For example, in some embodiments, the first actuator 2710, the second actuator 2720, or both can include any of the capstan assemblies or components described in U.S. Pat. No. 9,204,923 B2 (filed Jul. 16, 2008), entitled "Medical Instrument Electronically Energized Using Drive Cables," which is incorporated herein by reference in its entirety. In other embodiments, the first actuator 2710, the second actuator 2720, or both can include a linear actuator that pulls in or releases a cable. For example, in some embodiments, the first actuator 2710, the second actuator 2720, or both can be a linear actuator of the types described in U.S. Patent Application Pub. No. US2015/0047454 A1 (filed Aug. 15, 2014), entitled "Lever Actuated Gimbal Plate," or U.S. Pat. No. 6,817,974 B2 (filed Jun. 28, 2001), entitled "Surgical Tool Having Positively Positionable Tendon-Actuated Multi-Disk Wrist Joint," each of which is incorporated herein by reference in its entirety.

The cable guide 2800 is coupled to the housing 2760 and defines a shaft opening 2821, a first guide groove 2831, and a second guide groove 2832. The shaft opening 2821 is defined by an inner surface 2820 of the cable guide 2800 and opens into the passageway 2413 of the shaft 2410. As shown in FIG. 6, the shaft opening 2821 defines an opening center line $CL_{OP}$. Although shown as being parallel to, but non-coaxial with the shaft center line $CL_{SH}$, in other embodiments, the opening center line $CL_{OP}$ can be coaxial with (i.e., aligned with) the shaft center line $CL_{SH}$. In other embodiments, however, the opening center line $CL_{OP}$ can be nonparallel to the shaft center line $CL_{SH}$. The shaft opening 2821 need not be circular, but can have any suitable shape, as shown.

The first guide groove 2831 is defined by a first guide surface 2841 of the cable guide 2800 and defines a first guide center line $CL_1$. As shown, the first cable 2420 is routed within the first guide groove 2831, through the shaft opening 2821, and towards the shaft passageway 2413. The second guide groove 2832 is defined by a second guide surface 2842 of the cable guide 2800 and defines a second guide center line $CL_2$. The second cable 2430 is routed within the second guide groove 2832, through the shaft opening 2821 and towards the shaft passageway 2413. As shown in FIG. 5, the first guide groove 2831 and the second guide groove 2832 are splayed outward from the shaft opening 2821. Similarly stated, the first guide groove 2831 and the second guide groove 2832 are spread out apart from the shaft opening 2821. Said yet another way, the first guide groove 2831 and the second guide groove 2832 extend from the shaft opening 2821 and are nonparallel to each other. Specifically, the first guide center line $CL_1$ is nonparallel to the second guide center line $CL_2$. As shown in FIG. 5, the first guide center line $CL_1$ and the second guide center line $CL_2$ define a splay angle $\Theta$. The splay angle $\Theta$ can be any suitable value that facilitates alignment between the first actuator 2710 and the shaft opening 2821 and between the second actuator 2720 and the shaft opening 2821. The splay angle $\Theta$ can be, for example, between 5 degrees and 60 degrees, between 10 degrees and 45 degrees, or between 15 degrees and 30 degrees.

Although shown as being linear, in other embodiments, the first guide groove 2831, the second guide groove 2832, and any of the guide grooves described herein can be any suitable shape that allows for the first cable 2420 to be routed from the first actuator 2710 into the shaft opening 2821 and allows for the second cable 2430 to be routed the second actuator 2720 into the shaft opening 2821. In this manner, the first cable 2420 and the second cable 2430 can be routed into the desired position within the shaft opening 2821 (e.g., relative to the opening center line $CL_{OP}$ or the shaft center line $CL_{SH}$). Specifically, the first cable 2420 and the second cable 2430 can be positioned within the shaft passageway 2413 spaced apart from the shaft center line $CL_{SH}$ and at different radial or circumferential positions within the shaft passageway 2413. This arrangement can reduce the likelihood that the first cable 2420 will become entangled with (e.g., twisted about) the second cable 2430 within shaft 2410. For example, in some embodiments, the shaft 2410 can be configured to rotate about the shaft center line $CL_{SH}$ (e.g., in cases where shaft and portions of cables therein rotate about the shaft axis (which functions as a roll axis; the term roll is arbitrary). The cable guide 2800, and specifically the first guide groove 2831 and the second guide groove 2832 facilitate low-friction operation, including roll operation, by maintaining the first cable 2420 and the second cable 2430 within the shaft 2410 in their desired locations.

Referring to FIG. 6, the first guide center line $CL_1$ is nonparallel to the opening center line $CL_{OP}$. To facilitate this transition (or bend in the first cable 2420), the first guide surface 2841 includes a bend portion 2846 that transitions the first guide groove 2831 into the shaft opening 2821. The angle $\beta$ between the first guide center line $CL_1$ and the opening center line $CL_{OP}$ (referred to as the bend angle) can be any suitable value. For example, in some embodiments, the bend angle $\beta$ can be greater than 45 degrees. In other embodiments, the bend angle $\beta$ can be greater than 60 degrees. In yet other embodiments, the bend angle $\beta$ can be greater than 75 degrees.

In use, when the first actuator 2710 actuates the first cable 2420 (e.g., to cause movement of the first cable 2420), the first cable 2420 slides within the first guide groove 2831. Similarly, when the second actuator 2720 actuates the second cable 2430 (e.g., to cause movement of the second cable 2430), the second cable 2430 slides within the second guide groove 2832. Thus, the first cable 2420 slides against the first guide surface 2841 (including the bend portion 2846) and the second cable 2430 slides against the second guide surface 2842. In some embodiments, any of the guide surfaces described herein can be constructed from a low-friction material that reduces the frictional losses between the cables and the cable guide. For example, in some embodiments, the cable guide 2800 (and any of the cable guides described herein) can be monolithically constructed from a low friction material. Such materials can include, for example, polyether ether ketone (PEEK) filled with at least one of a glass material or polytetrafluoroethylene (PTFE). In some embodiments, the cable guide 2800 (and any of the cable guides described herein) can be monolithically constructed from any suitable material (e.g., polymer, metal, composite) and can include a friction-reducing coating on the guide surfaces (e.g., the first guide surface 2841, including the bend portion 2846). In yet other embodiments, the cable guide 2800 (and any of the cable guides described herein) can be constructed from separate components that are assembled to form the cable guide 2800. For example, in some embodiments, the cable guide 2800 (and any of the cable guides described herein) can include a bend portion (e.g., the bend portion 2846) that is a separate component coupled to the remainder of the cable guide. Although the bend portion 2846 is shown and described as being in a fixed position (i.e., it does not move) relative the cable guide 2800, in other embodiments, the cable guide 2800 (and any of the cable guides described herein) can include one or more bearings or rollers captively coupled within a guide groove (e.g., the first guide groove 2831) to reduce the friction when the cable slides against the cable guide.

Figure 7:
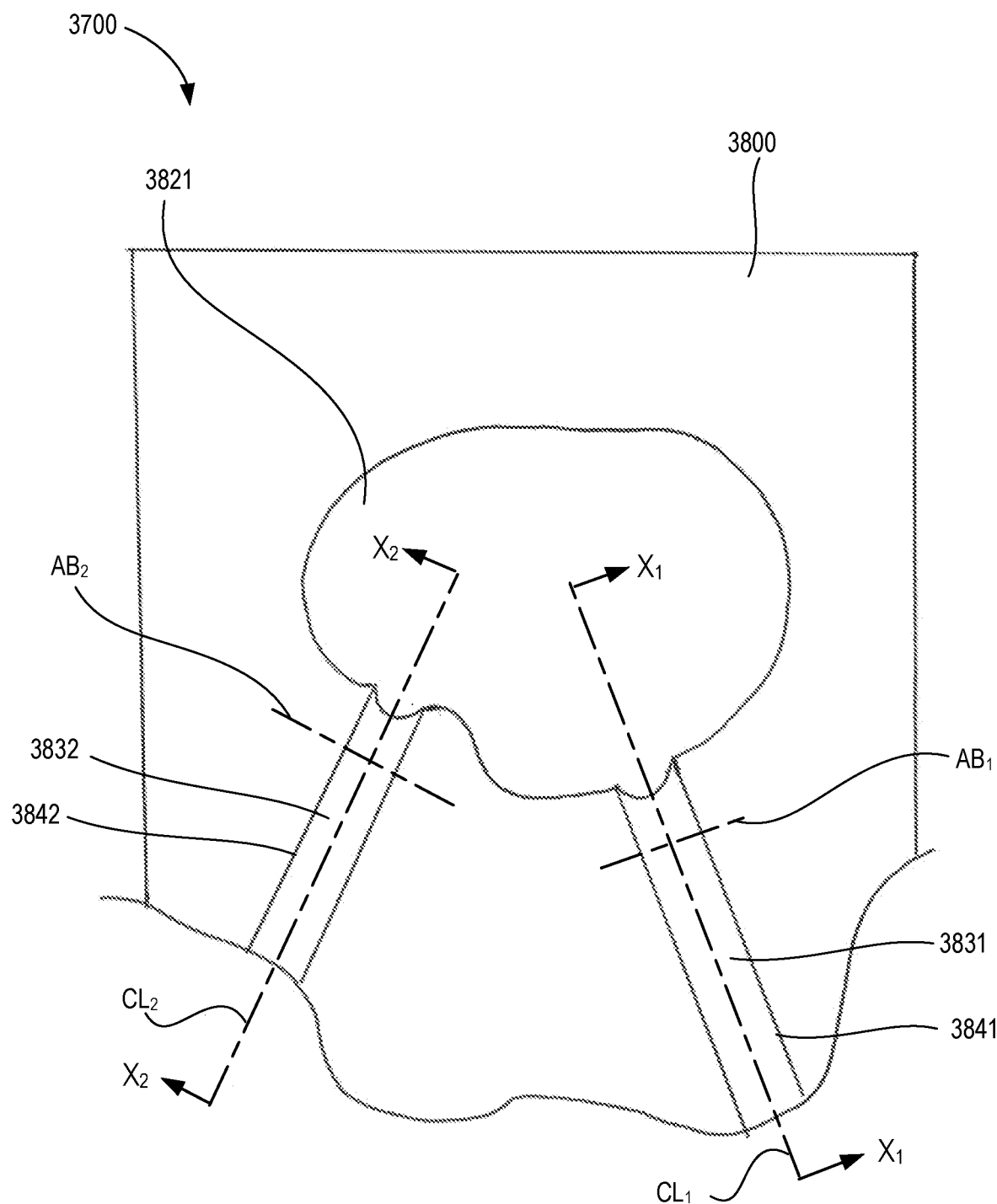
FIG. 7 is a diagrammatic top view of a portion of an instrument of a surgery system in a first position, according to an embodiment.
Figure 8:
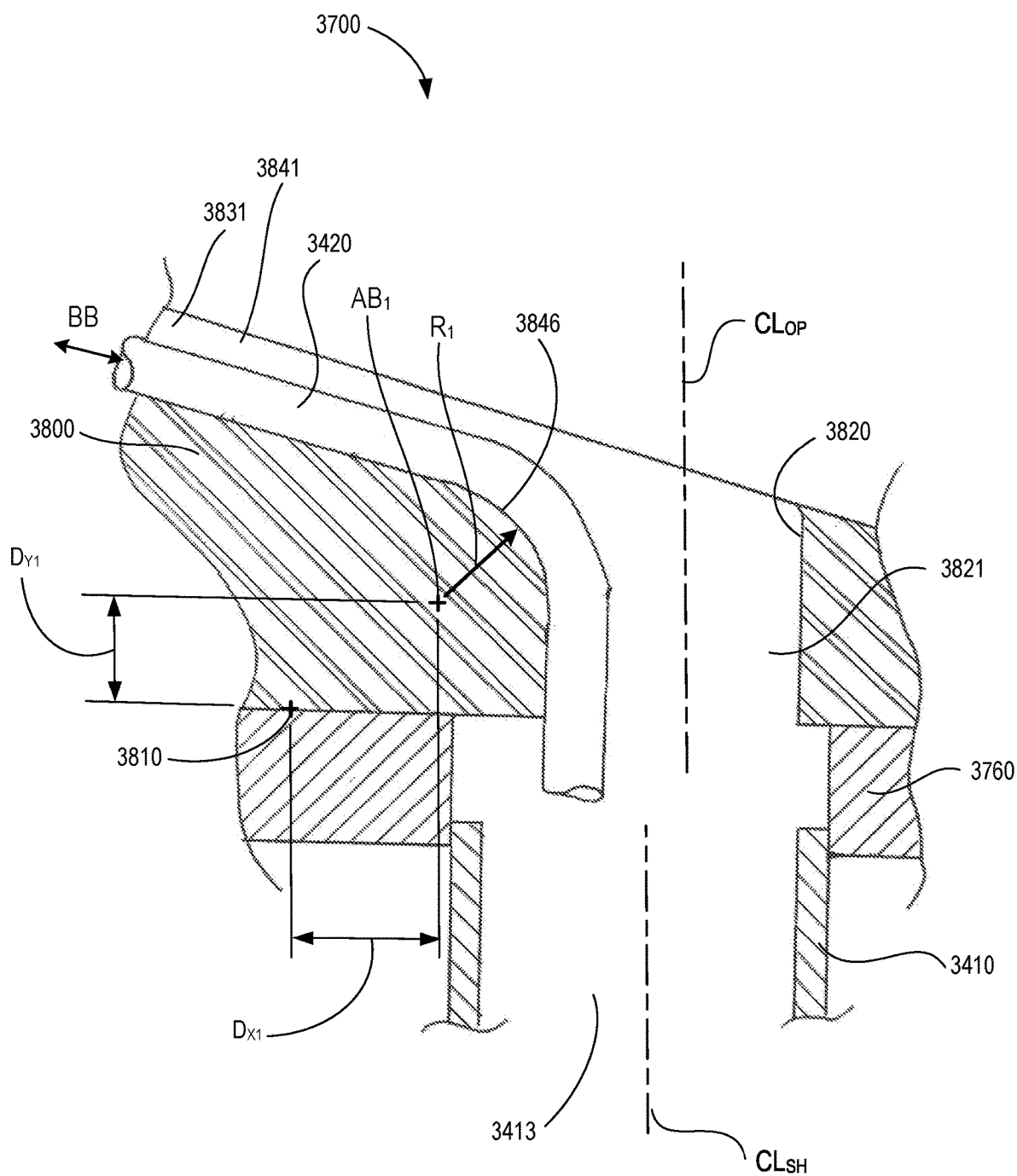
FIG. 8 is a diagrammatic side view of the portion of the instrument shown in FIG. 7 taken along line $X_1$-$X_1$ in FIG. 7.
Figure 9:
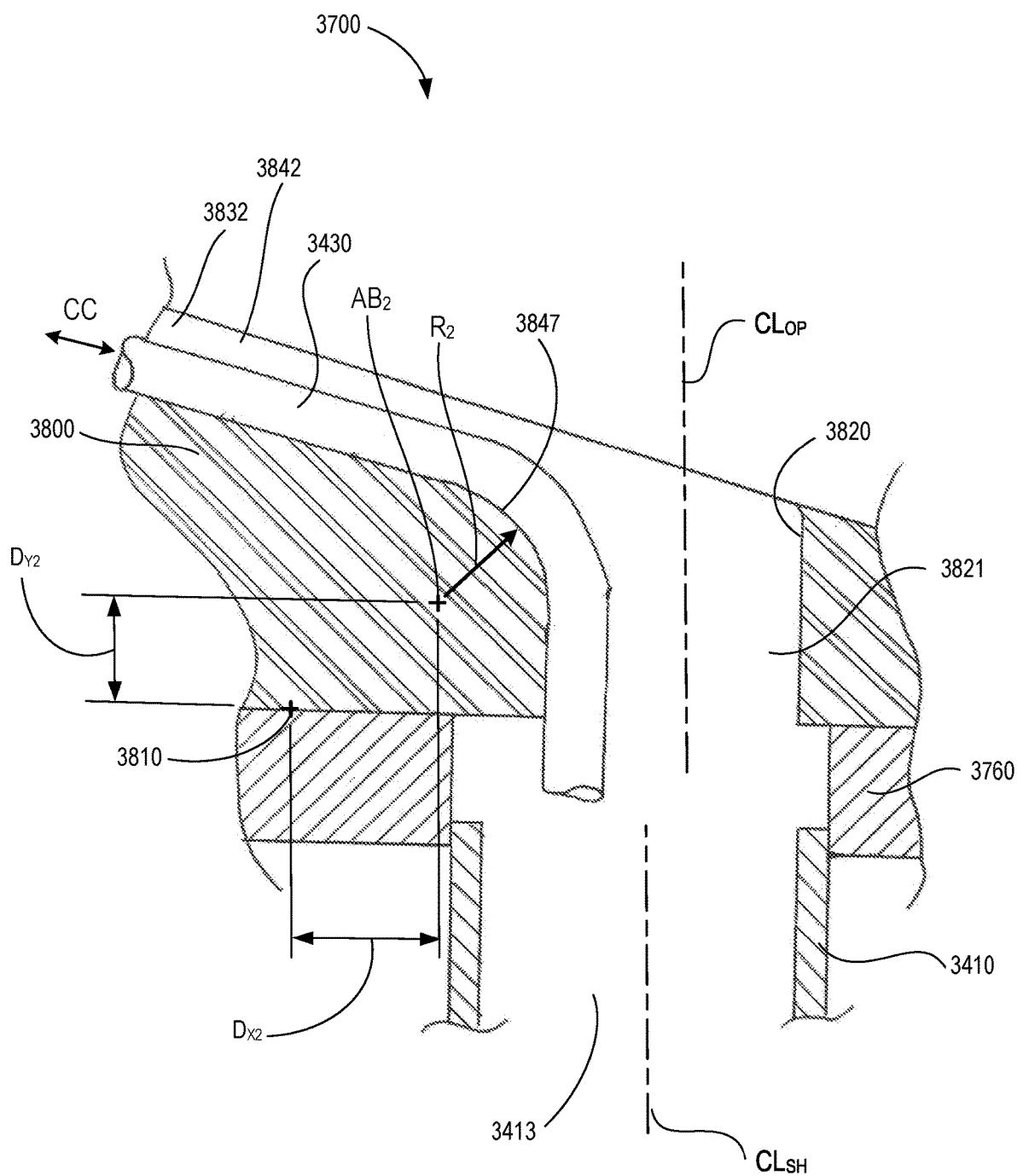
FIG. 9 is a diagrammatic side view of the portion of the instrument shown in FIG. 7 taken along line $X_2$-$X_2$ in FIG. 7.
Figure 10:
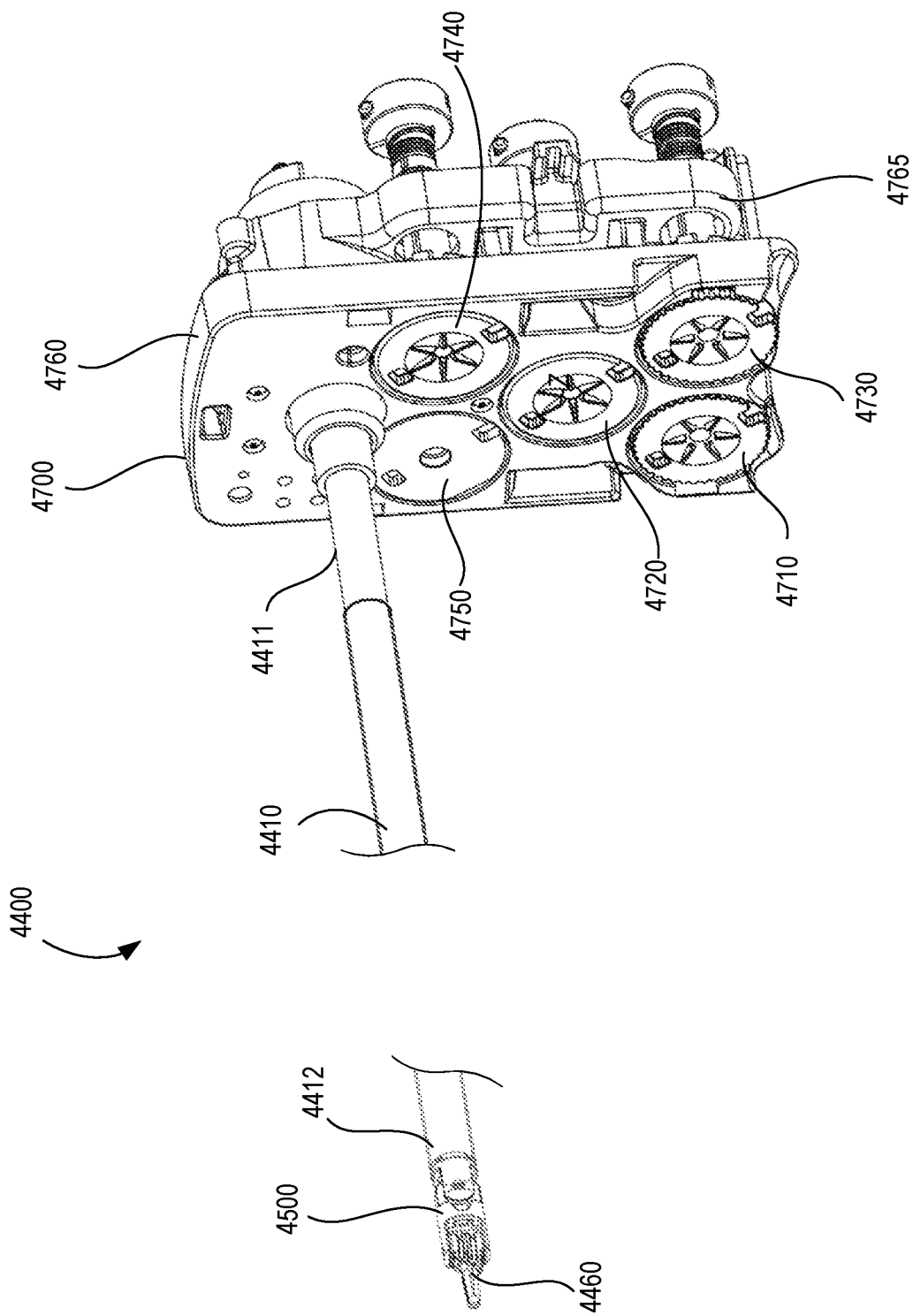
FIG. 10 is a perspective view of an instrument of a surgery system, according to an embodiment.

In some embodiments, a cable guide can include multiple guide grooves, each having a bend portion that transitions each guide groove into a shaft opening, a shaft passageway, or both a shaft opening or a shaft passageway. Moreover, in such embodiments, the bend portions can form a curvature about a bend axis and each bend axis can be nonparallel to another bend axis. For example, FIGS. 7-9 are diagrammatic illustrations of various portions of a transmission 3700, according to an embodiment. The transmission 3700 can be included in any of the instruments shown and described herein (e.g., the instrument 4400) and can function as an actuator to move one or more tensions members (e.g., the first cable 3420, see FIG. 8, and the second cable 3430, see FIG. 9) to actuate any suitable end effector. In some embodiments, the transmission 3700 or any of the components therein are optionally parts of a surgical system that performs minimally invasive surgical procedures and which can include a manipulator unit, a series of kinematic linkages, a series of cannulas, or the like. The transmission 3700 (and any of the instruments described herein) can be used in any suitable surgical system, such as the MIRS system 1000 shown and described above. The transmission 3700 includes a chassis 3760 and a cable guide 3800.

The chassis 3760 (which functions as a housing) provides the structural support for mounting and aligning the components of the transmission 3700. For example, as shown in FIGS. 8 and 9, the chassis 3760 is coupled to a shaft 3410 of a medical instrument. The shaft 3410 can be any suitable elongated shaft that couples a wrist assembly, end effector, or other component (not shown) to the transmission 3700. Specifically, the shaft 3410 includes a proximal end portion that is coupled to the chassis 3760. The shaft 3410 defines at least one passageway 3413 through which the first cable 3420, the second cable 3430, and other components (e.g., energized electrical wires, ground wires, or the like, not shown in FIGS. 7-9) can be routed from the transmission 3700 towards a wrist assembly, end effector, or other component. Although shown as including a single passageway 3413 that defines a shaft center line $CL_{SH}$, in other embodiments, the shaft 3410 can define multiple passageways. Moreover, although the chassis 3760 is shown as defining an opening within which the proximal end portion of an instrument shaft 3410 is mounted, in other embodiments, the shaft 3410 can be coupled to the chassis 3760 by any suitable mechanism (e.g., a flange connection).

The chassis 3760 also provides support structure and mounting structure to which one or more actuators (not shown, but which can be similar to the first actuator 2710 or the second actuator 2720 described above). Specifically, the one or more actuators can be any suitable actuator that can apply a force to or move the first cable 3420, the second cable 3430, or both. Movement of the first cable 3420 is shown by the arrow BB in FIG. 8, and movement of the second cable 3430 is shown by the arrow CC in FIG. 9. In addition to providing mounting support for the internal components of the transmission 3700, the chassis 3760 can also include external features (not shown, but which can be recesses, clips, etc.) that interface with a docking port of a drive device (not shown). The drive device can be, for example, a computer-assisted teleoperated surgical system that can receive the transmission 3700 and manipulate the transmission 3700 to perform various surgical operations. In other embodiments, the drive device can be an assembly system that can receive and manipulate the transmission 3700 to perform various assembly operations.

The cable guide 3800 is coupled to the housing 3760 and defines a shaft opening 3821, a first guide groove 3831, and a second guide groove 3832. The cable guide 3800 can be coupled to the housing 3760 by any suitable mechanism. For example, as shown the cable guide 3800 includes a mounting portion 3810 that is coupled to the housing 3760. The mounting portion 3810 can be any portion or structure that engages the housing 3760, such as a protrusion, a recess, a shoulder, or a fastener. In this manner, the mounting portion 3810 indexes the cable guide 3800 to the housing 3760 (and therefore the shaft 3410) to ensure that the shaft opening 3821 is aligned with the shaft 3410 as desired.

The shaft opening 3821 is defined by an inner surface 3820 of the cable guide 3800 and opens into the passageway 3413 of the shaft 3410. As shown in FIGS. 8 and 9, the shaft opening 3821 defines an opening center line $CL_{OP}$. Although shown as being parallel to, but noncoaxial with the shaft center line $CL_{SH}$, in other embodiments, the opening center line $CL_{OP}$ can be coaxial with (i.e., aligned with) the shaft center line $CL_{SH}$. In other embodiments, however, the opening center line $CL_{OP}$ can be nonparallel to the shaft center line $CL_{SH}$. The shaft opening 3821 need not be circular, but can have any suitable shape, as shown.

Referring to FIG. 8, the first guide groove 3831 is defined by a first guide surface 3841 of the cable guide 3800 and defines a first guide center line $CL_1$. As shown, the first cable 3420 is routed within the first guide groove 3831, through the shaft opening 3821, and towards the shaft passageway 3413. The first guide surface 3841 includes a first bend portion 3846 transitioning from the first guide groove 3831 into the shaft opening 3821. The first bend portion 3846 is characterized by a first bend radius $R_1$ about a first bend axis $AB_1$. The first bend axis $AB_1$ is offset from the mounting portion 3810 by a first distance. Specifically, the first bend axis $AB_1$ is offset from the mounting portion 3810 by a first vertical distance $D_{Y1}$ and a first horizontal distance $D_{X1}$. In this manner, the location of the first bend axis $AB_1$ relative to the shaft passageway 3413 is indexed. The bend angle (i.e., the angle between the first guide center line $CL_1$ and the opening center line $CL_{OP}$) can be any suitable value. For example, in some embodiments, the bend angle can be greater than 45 degrees. In other embodiments, the bend angle can be greater than 60 degrees. In yet other embodiments, the bend angle can be greater than 75 degrees.

Referring to FIG. 9, the second guide groove 3832 is defined by a second guide surface 3842 of the cable guide 3800 and defines a second guide center line $CL_2$. As shown, the second cable 3430 is routed within the second guide groove 3832, through the shaft opening 3821 and towards the shaft passageway 3413. The second guide surface 3842 includes a second bend portion 3847 transitioning from the second guide groove 3832 into the shaft opening 3821. The second bend portion 3847 is characterized by a second bend radius $R_2$ about a second bend axis $AB_2$. The second bend axis $AB_2$ is offset from the mounting portion 3810 by a first distance. Specifically, the second bend axis $AB_2$ is offset from the mounting portion 3810 by a second vertical distance $D_{Y2}$ and a second horizontal distance $D_{X2}$. In this manner, the location of the second bend axis $AB_2$ relative to the shaft passageway 3413 is indexed. The bend angle (i.e., the angle between the second guide center line $CL_2$ and the opening center line $CL_{OP}$) can be any suitable value. For example, in some embodiments, the bend angle can be greater than 45 degrees. In other embodiments, the bend angle can be greater than 60 degrees. In yet other embodiments, the bend angle can be greater than 75 degrees.

As shown in FIG. 7, the first bend axis $AB_1$ is nonparallel to the second bend axis $AB_2$. This arrangement allows the first guide groove 3831 and the second guide groove 3832 to be splayed outward from the shaft opening 3821. Moreover, in some embodiments, the first bend axis $AB_1$ and the second bend axis $AB_2$ can be offset from the mounting surface by different distances. For example, in some embodiments, the first vertical distance $D_{Y1}$ can be greater than the second vertical distance $D_{Y2}$. With this arrangement, the first bend portion 3846 is positioned higher than (relative to the shaft 3410) than the second bend portion 3847. In other embodiments, the first horizontal distance $D_{X1}$ can be greater than the second horizontal distance $D_{X2}$. With this arrangement, the first bend portion 3846 is positioned closer towards the shaft center line $CL_{SH}$ than is the second bend portion 3847. In this manner, the first cable 3420 and the second cable 3430 can be routed into the desired position within the shaft opening 3821 (e.g., relative to the opening center line $CL_{OP}$ or the shaft center line $CL_{SH}$). Specifically, the first cable 3420 and the second cable 3430 can be positioned within the shaft passageway 3413 spaced apart from the shaft center line $CL_{SH}$ and at different radial or circumferential positions within the shaft passageway 3413. This arrangement can reduce the likelihood that the first cable 3420 will become entangled with (e.g., twisted about) the second cable 3430 within shaft 3410. For example, in some embodiments, the shaft 3410 can be configured to rotate about the shaft center line $CL_{SH}$ (e.g., in cases where shaft and portions of cables therein rotate about the shaft axis (which functions as a roll axis; the term roll is arbitrary). The cable guide 3800, and specifically the first guide groove 3831 and the second guide groove 3832 facilitates low-friction operation, including roll operation, by maintaining the first cable 3420 and the second cable 3430 within the shaft 3410 in their desired locations.

In some embodiments, the first bend radius $R_1$ can be the same size as the second bend radius $R_2$. In other embodiments, the first bend radius $R_1$ can be a different size as the second bend radius $R_2$. Moreover, in some embodiments, either of the first bend portion 3846 or the second bend portion 3847 can be characterized by any suitable curved shape, including a non-circular shape that is constructed from multiple different bend radii.

In use, when the first actuator 3710 actuates the first cable 3420 (e.g., to cause movement of the first cable 3420, as shown by the arrow BB), the first cable 3420 slides within the first guide groove 3831. Similarly, when the second actuator 3720 actuates the second cable 3430 (e.g., to cause movement of the second cable 3430, as shown by the arrow CC), the second cable 3430 slides within the second guide groove 3832. Thus, the first cable 3420 slides against the first guide surface 3841 (including the first bend portion 3846), and the second cable 3430 slides against the second guide surface 3842 (including the second bend portion 3847).

Although the transmission 2700 and the transmission 3700 are each shown and described as including only two tension members (e.g., the first cable 2420 and the second cable 2430), in other embodiments, a transmission or an instrument can include any suitable number of tension members. For example, in some embodiments, an instrument can include four tension members (or portions of tension members) or six tension members (or portions of tension members). For example, FIGS. 10-17 are various views of an instrument 4400 (and portions of the instrument 4400), according to an embodiment. In some embodiments, the instrument 4400 or any of the components therein are optionally parts of a surgical assembly that performs minimally invasive surgical procedures and which can include a manipulator unit, a series of kinematic linkages, a series of cannulas, or the like. The instrument 4400 (and any of the instruments described herein) can be used in any suitable surgical system, such as the MIRS system 1000 shown and described above. The instrument 4400 includes a transmission 4700 (that can function as an actuator mechanism), an instrument shaft 4410, a wrist assembly 4500, and an end effector 4460.

Figure 11:
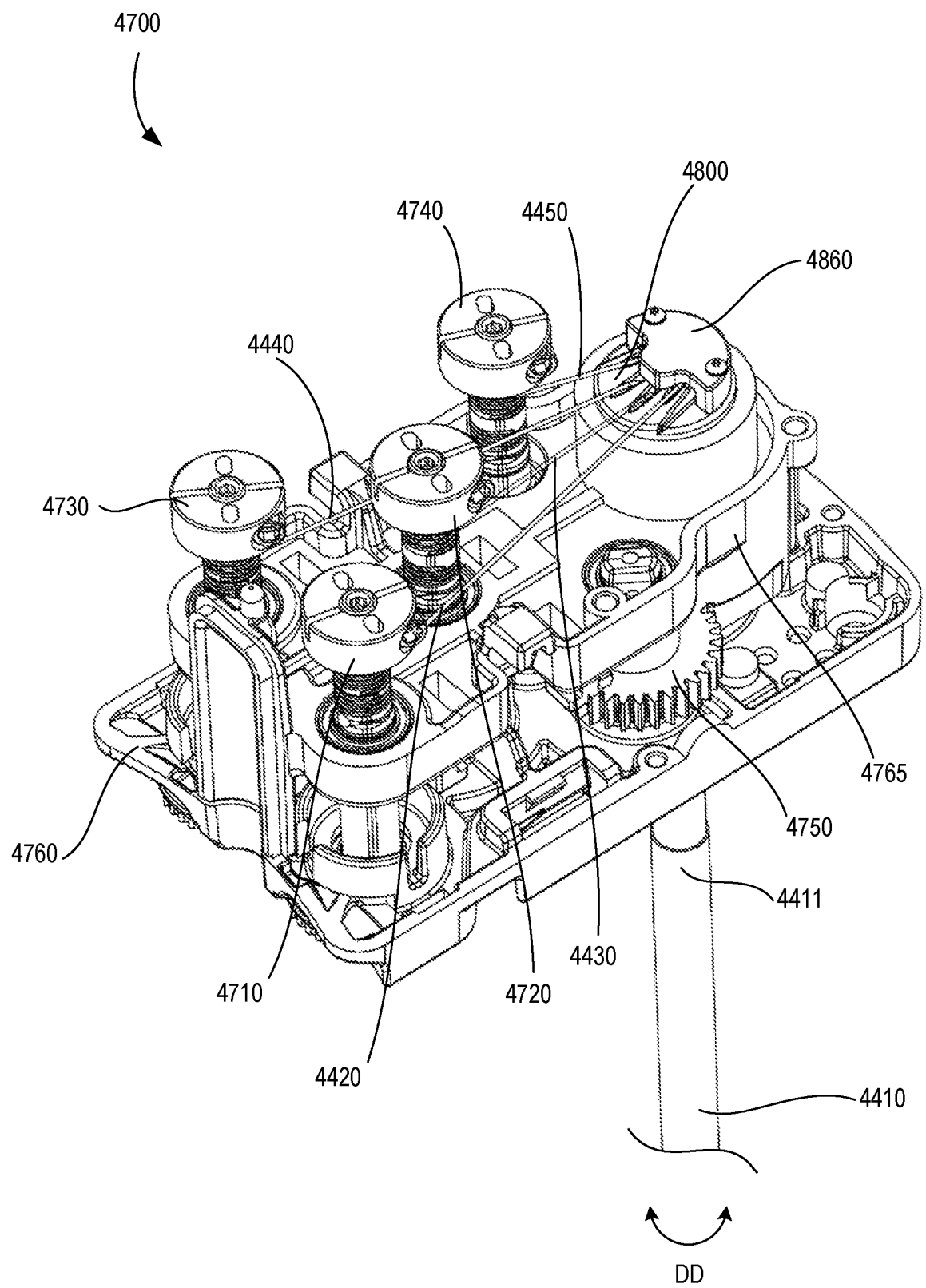
FIGS. 11 and 12 are enlarged perspective views of a transmission at the proximal end portion of the instrument shown in FIG. 10.
Figure 12:
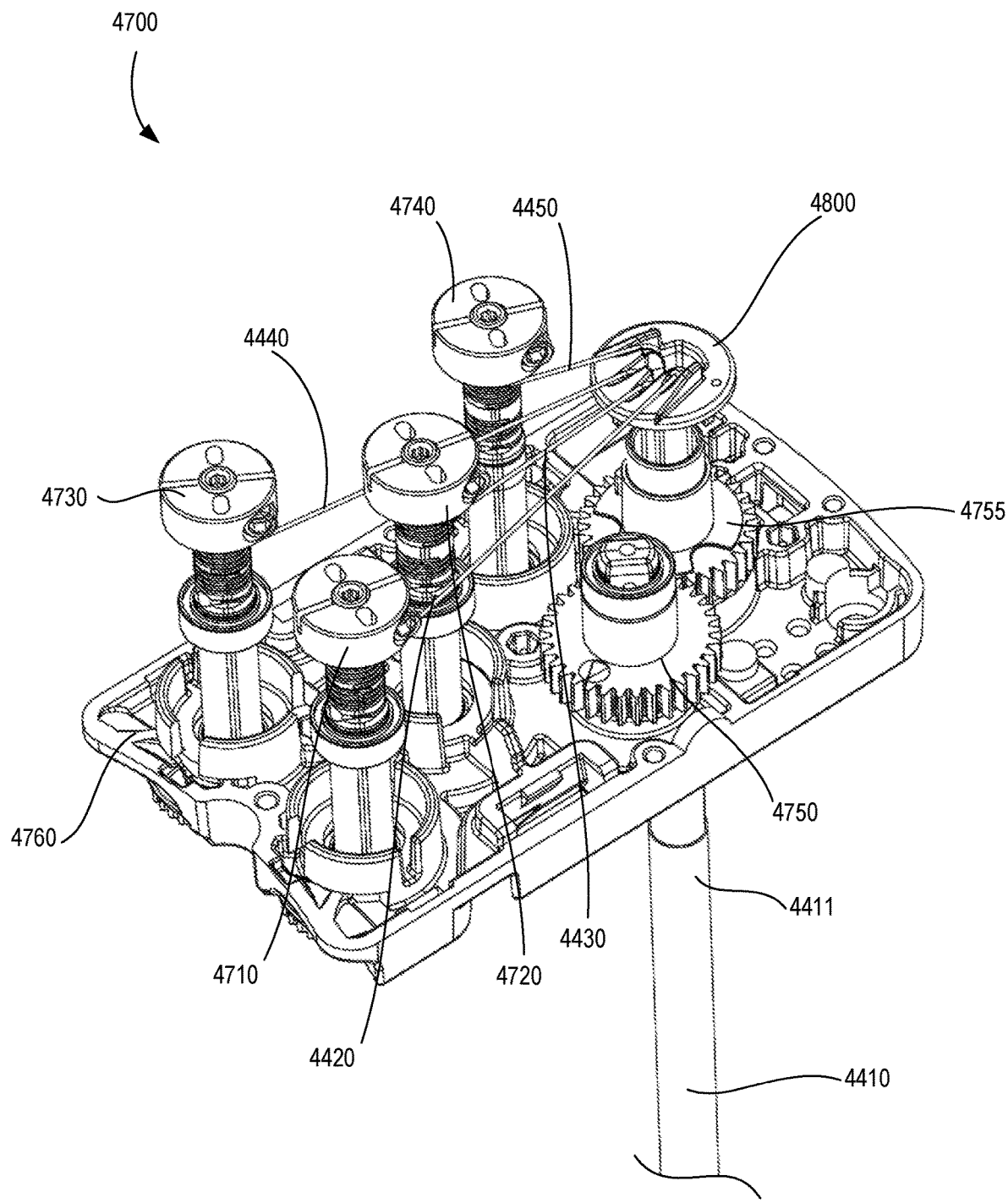

Referring to FIG. 11, the instrument 4400 also includes a first cable 4420 (which functions as a tension member), a second cable 4430 (which functions as a tension member), a third cable 4440 (which functions as a tension member), and a fourth cable 4450 (which functions as a tension member) that couple the transmission 4700 to the wrist assembly 4500. The instrument 4400 is configured such that movement of the tension members can produce rotation of the wrist assembly 4500 (i.e., pitch rotation), yaw rotation of the end effector 4460, grip rotation of the tool members of the end effector 4460 about the yaw axis, or any combination of these movements. Changing the pitch, yaw, or grip of the instrument 4400 can be performed by manipulating the four tension members.

The transmission 4700 produces movement of each of the first tension member 4420 and the second tension member to produce the desired movement (pitch, yaw, or grip) at the wrist assembly 4500. Specifically, the transmission 4700 includes components and controls to move some of the tension members in a proximal direction (i.e., to pull in certain tension members) while simultaneously allowing the distal movement (i.e., releasing or "paying out") of other of the tension members. In this manner, the transmission 4700 can maintain the desired tension within the tension members, and, in some embodiments, can ensure that the lengths of the tension members are conserved (i.e., moved in equal amounts) during the entire range of motion of the wrist assembly 4500.

The transmission 4700 includes a chassis 4760, a first capstan assembly 4710, a second capstan assembly 4720, a third capstan assembly 4730, a fourth capstan assembly 4740, a roll actuator 4750, and a cable guide 4800. The chassis 4760 (which functions as a housing) provides the structural support for mounting and aligning the components of the transmission 4700. For example, as shown in FIG. 11, the chassis 4760 defines a first opening within which the proximal end portion 4411 of the shaft 4410 is mounted, and multiple second openings within which the capstan assemblies are mounted. The chassis 4760 includes an upper housing 4765 that provides additional mounting surfaces and support (e.g., for the capstan assemblies).

The shaft 4410 can be any suitable elongated shaft that couples the wrist assembly 4500 and the end effector 4460 to the transmission 4700. Specifically, the shaft 4410 includes a proximal end portion 4411 that is coupled to the chassis 4760. The shaft 4410 defines at least one passageway through which the first cable 4420, the second cable 4430, the third cable 4440, the fourth cable 4450, and other components (e.g., energized electrical wires, ground wires, or the like, not shown) can be routed from the transmission 4700 towards the wrist assembly 4500. Moreover, although the chassis 4760 is shown as defining an opening within which the proximal end portion of an instrument shaft 4410 is mounted, in other embodiments, the shaft 4410 can be coupled to the chassis 4760 by any suitable mechanism (e.g., a flange connection).

In addition to providing mounting support for the internal components of the transmission 4700, the chassis 4760 can also include external features (not shown, but which can be recesses, clips, etc.) that interface with a docking port of a drive device (not shown). The drive device can be, for example, a computer-assisted teleoperated surgical system that can receive the transmission 4700 and manipulate the transmission 4700 to perform various surgical operations. In other embodiments, the drive device can be an assembly system that can receive and manipulate the transmission 4700 to perform various assembly operations.

The first capstan assembly 4710 includes a shaft that can be motor-driven to rotate about a capstan axle. The rotating shaft includes a portion about which an end portion of the first cable 4420 is wrapped. Thus, when the first capstan assembly 4710 rotates in a first direction, the first cable 4420 can be moved proximally (i.e., can be pulled inward or wrapped about the rotating shaft), and when the first capstan assembly 4710 rotates in a second direction, the first cable 4420 can be moved distally (i.e., can be payed-out or unwrapped from the rotating shaft). In a similar manner, the second capstan assembly 4720 includes a shaft about which an end portion of the second cable 4430 is wrapped, the third capstan assembly 4730 includes a shaft about which an end portion of the third cable 4440 is wrapped, and the fourth capstan assembly 4740 includes a shaft about which an end portion of the fourth cable 4450 is wrapped. Referring to FIG. 11, the arrangement of the capstan assemblies and the cable guide 4800 defines a cable path for each of the cables.

Through these cable paths, the cables are routed from their respective capstan assembly into the shaft 4410.

The roll actuator 4750 includes a shaft that can be motor-driven to rotate about an axle. The rotating shaft includes a gear that meshes with a shaft gear 4755 (see FIG. 17) coupled to the shaft 4410. Thus, when the roll actuator 4750 rotates in a first direction, the shaft gear 4755 (and thus the shaft 4410) can be rotated in a first direction, and when the roll actuator 4750 rotates in a second direction, the shaft gear 4755 can be rotated in a second direction. The rotation of the shaft about the shaft axis (which functions as a roll axis; the term roll is arbitrary) is shown by the arrow DD in FIGS. 11 and 17.

Figure 17:
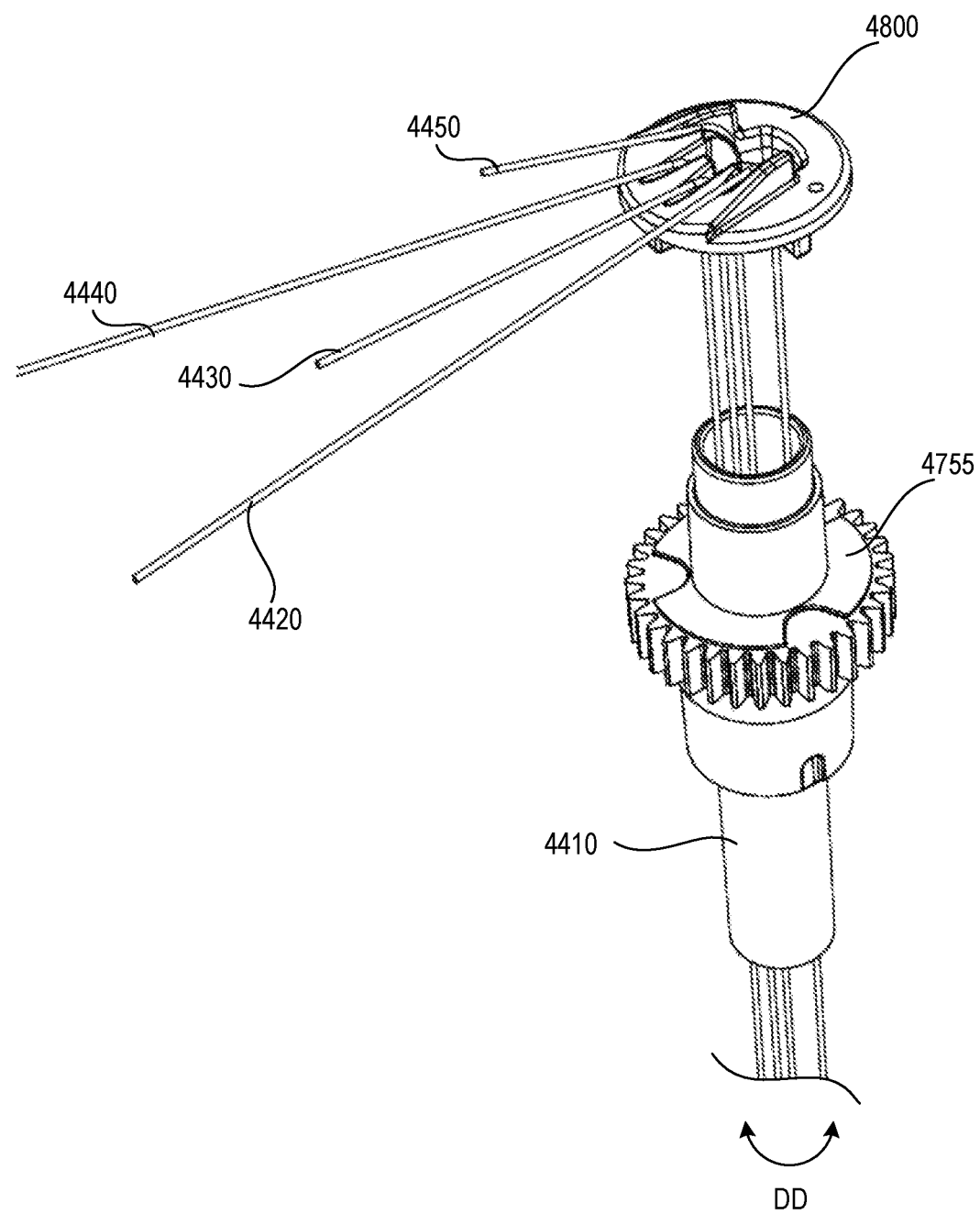
FIG. 17 is an exploded perspective view of the cable guide, the cables, and a portion of the shaft drive assembly of the transmission shown in FIGS. 11 and 12.

The cable guide 4800 includes a cable cover 4860 and is coupled to the upper housing 4765 of the chassis 4760. Specifically, the cable guide 4800 and the cable cover 4860 are coupled to the upper housing 4765 by two screws. In other embodiments, the cable guide 4800 and the cable cover 4860 can be coupled to the upper housing 4765 by any suitable mechanism (e.g., adhesive, heat weld, or the like). For example, in some embodiments, the cable cover 4860 can be coupled to the cable guide 4800 via screws, and the cable guide 4800 can be coupled to the upper housing 4765 by an adhesive. The cable guide 4800 includes an inner surface 4820 that defines a shaft opening 4821. As shown in FIG. 17, the shaft opening 4821 opens into the passageway 4413 of the shaft 4410. Moreover, although shown as being noncircular, the shaft opening 4821 can have any suitable shape (e.g., circular, oblong, or elliptical).

The cable guide 4800 includes a top surface 4830 defining a first guide groove 4831, a second guide groove 4832, a third guide groove 4833, and a fourth guide groove 4834. The first cable 4420 is routed within the first guide groove 4831, through the shaft opening 4821, and towards the shaft passageway. The first guide groove 4831 is defined by a first guide surface 4841 and defines a first guide center line (not identified). The first guide surface 4841 includes a first bend portion 4846 transitioning from the first guide groove 4831 into the shaft opening 4821. The first bend portion 4846 is characterized by a first bend radius about a first bend axis (the first bend radius and the first bend axis are not identified, but are like the bend radius $R_1$ and the bend axis $AB_1$ described above with respect to the cable guide 3800). The second cable 4430 is routed within the second guide groove 4832, through the shaft opening 4821, and towards the shaft passageway. The second guide groove 4832 is defined by a second guide surface 4842, and defines a second guide center line (not identified). The second guide surface 4842 includes a second bend portion 4847 transitioning from the second guide groove 4832 into the shaft opening 4821. The second bend portion 4847 is characterized by a second bend radius about a second bend axis (the second bend radius and the second bend axis are not identified, but are like the bend radius $R_2$ and the bend axis $AB_2$ described above with respect to the cable guide 3800). The third cable 4440 is routed within the third guide groove 4833, through the shaft opening 4821 and towards the shaft passageway. The third guide groove 4833 is defined by a third guide surface 4843, and defines a third guide center line (not identified). The third guide surface 4843 includes a third bend portion 4848 transitioning from the third guide groove 4833 into the shaft opening 4821. The third bend portion 4848 is characterized by a third bend radius about a third bend axis (the third bend radius and the third bend axis are not identified, but are like the bend radii and the bend axes described above with respect to the cable guide 3800). The fourth cable 4450 is routed within the fourth guide groove 4834, through the shaft opening 4821 and towards the shaft passageway. The fourth guide groove 4834 is defined by a fourth guide surface 4844, and defines a fourth guide center line (not identified). The fourth guide surface 4844 includes a fourth bend portion 4849 transitioning from the fourth guide groove 4834 into the shaft opening 4821. The fourth bend portion 4849 is characterized by a fourth bend radius about a fourth bend axis (the fourth bend radius and the fourth bend axis are not identified, but are like the bend radii and the bend axes described above with respect to the cable guide 3800).

Figure 13:
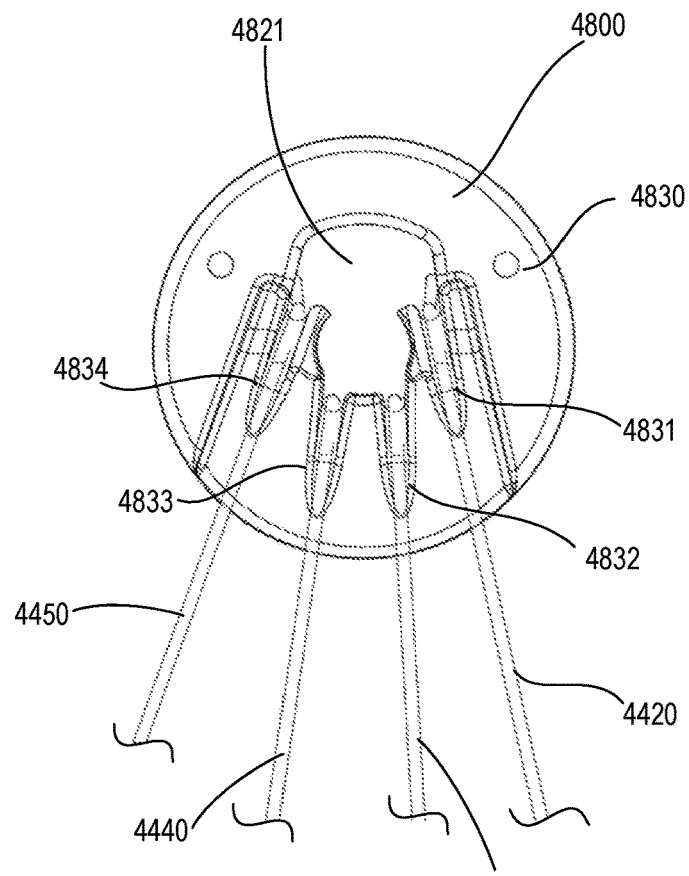
FIG. 13 is a top view of a cable guide and the cables of the transmission shown in FIGS. 11 and 12.
Figure 14:
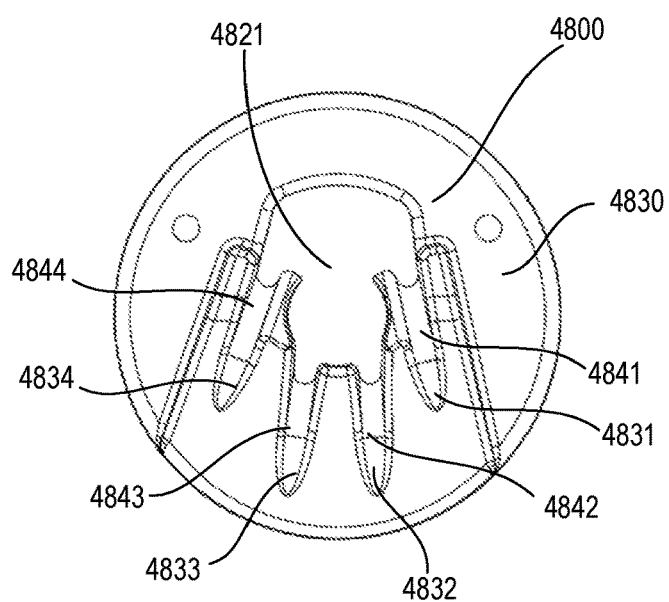
FIGS. 14 and 15 are a top view (FIG. 14) and a top perspective view (FIG. 15) of the cable guide of the transmission shown in FIGS. 11 and 12.
Figure 15:
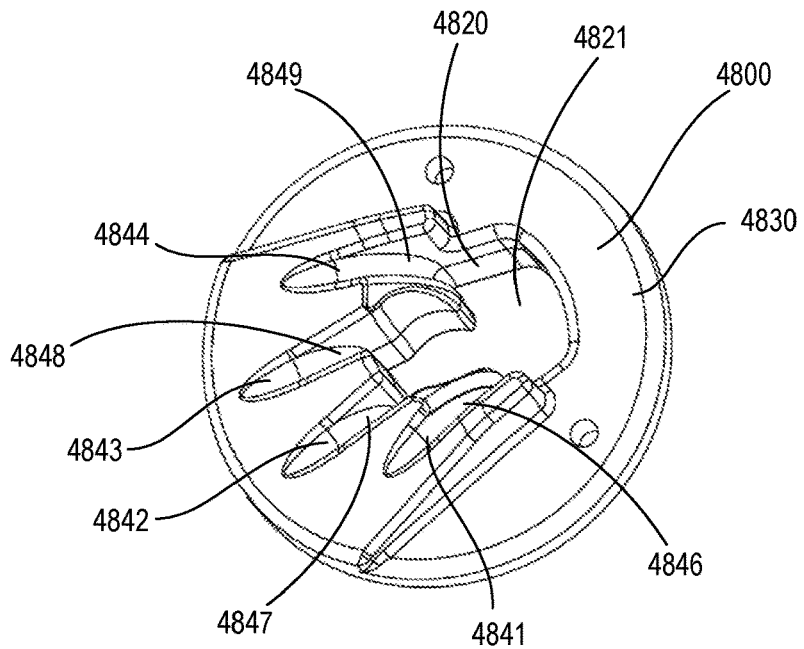
Figure 16:
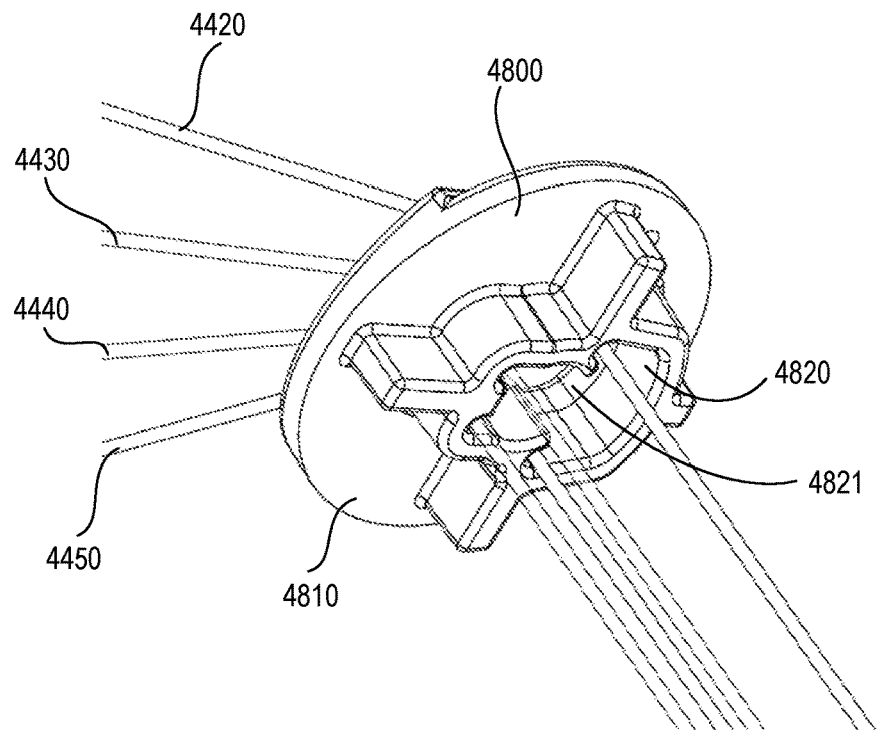
FIG. 16 is a bottom perspective view of the cable guide and the cables of the transmission shown in FIGS. 11 and 12.

As shown in FIGS. 13 and 14, the first guide groove 4831, the second guide groove 4832, the third guide groove 4833, and the fourth guide groove 4834 are splayed outward from the shaft opening 4821. Similarly stated, the guide grooves are spread out apart from the shaft opening 4821. Although not identified in FIGS. 13 and 14, the guide grooves can define any suitable splay angle between them (similar to the splay angle Θ described above with reference to the cable guide 2800). For example, the splay angle between adjacent guide grooves can be, for example, between 5 degrees and 60 degrees, between 10 degrees and 45 degrees, or between 15 degrees and 30 degrees. Additionally, the bend axes can be nonparallel to any of the other bend axes. For example, the first bend axis is nonparallel to the second bend axis, the third bend axis, and the fourth bend axis. This arrangement allows the guide grooves to be splayed outward from the shaft opening 4821, as described above. All four of the bend axes, however, need not be nonparallel to each of the other bend axes. For example, in some embodiments, the second bend axis and the third bend axis can be parallel.

In some embodiments, at least one bend axis can be offset from a mounting surface of the cable guide (not shown) by a different distance than an offset distance from other of the bend axes. For example, as described above with respect to the cable guide 3800, in some embodiments, the first bend portion 4846 can be positioned higher than (relative to the shaft 4410) than the second bend portion 4847 (or other of the bend portion). In other embodiments, the first bend portion 4846 can be positioned closer towards the shaft center line $CL_{SH}$ than the second bend portion 4847 (or other of the bend portions). In this manner, the first cable 4420, the second cable 4430, the third cable 4440, and the fourth cable 4450 can be routed into the desired position within the shaft opening 4821. Specifically, the cables can be positioned within the shaft passageway spaced apart from the shaft center line and at different radial or circumferential positions within the shaft passageway. This arrangement can reduce the likelihood that the cables will become entangled with (e.g., twisted about) each other within shaft 4410. For example, this arrangement facilitates low-friction operation during roll of the shaft 4410 by maintaining the cables within the shaft 4410 in their desired locations.

Figure 18:
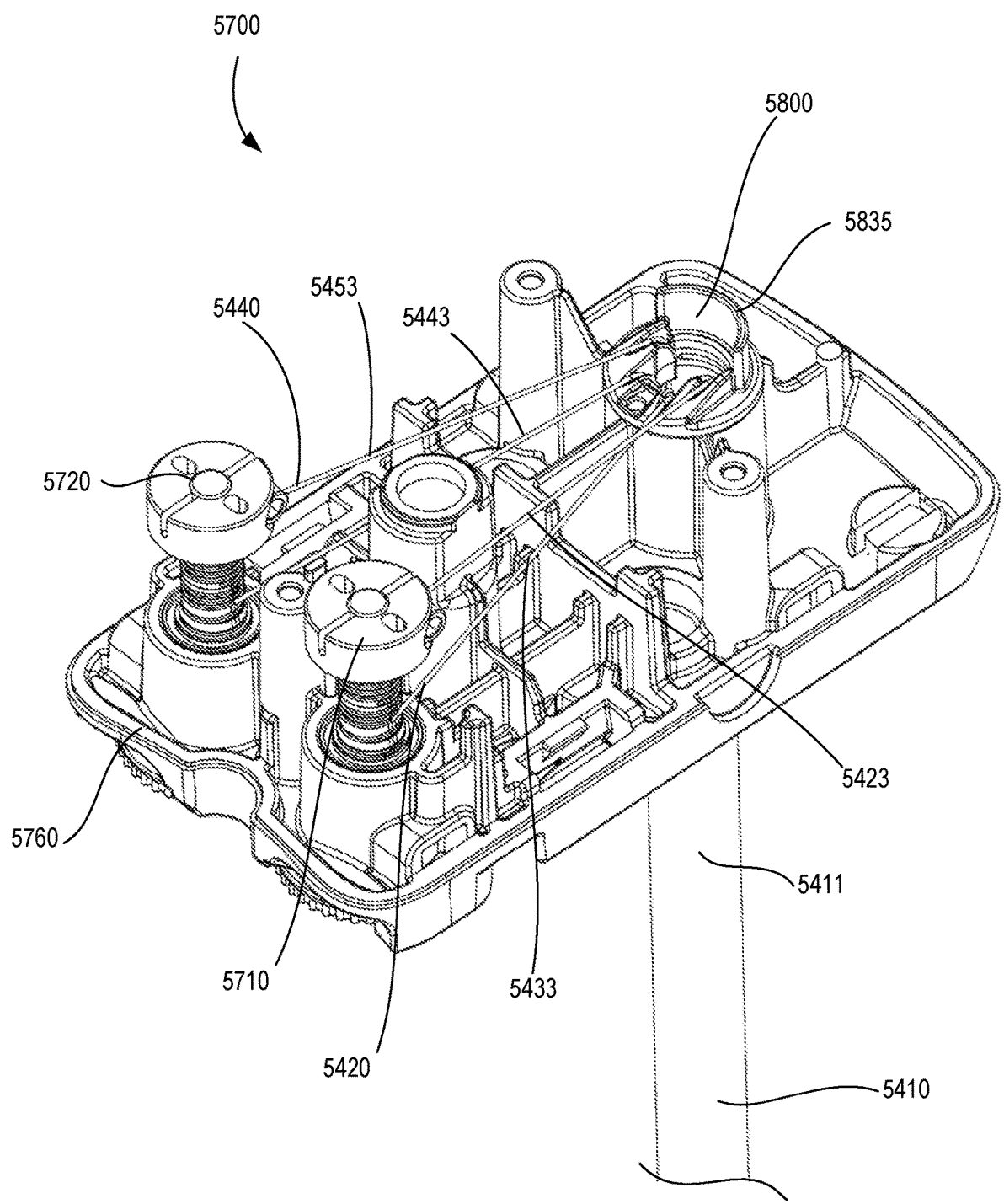
FIG. 18 is a perspective view of a transmission of an instrument, according to an embodiment.
Figure 19:
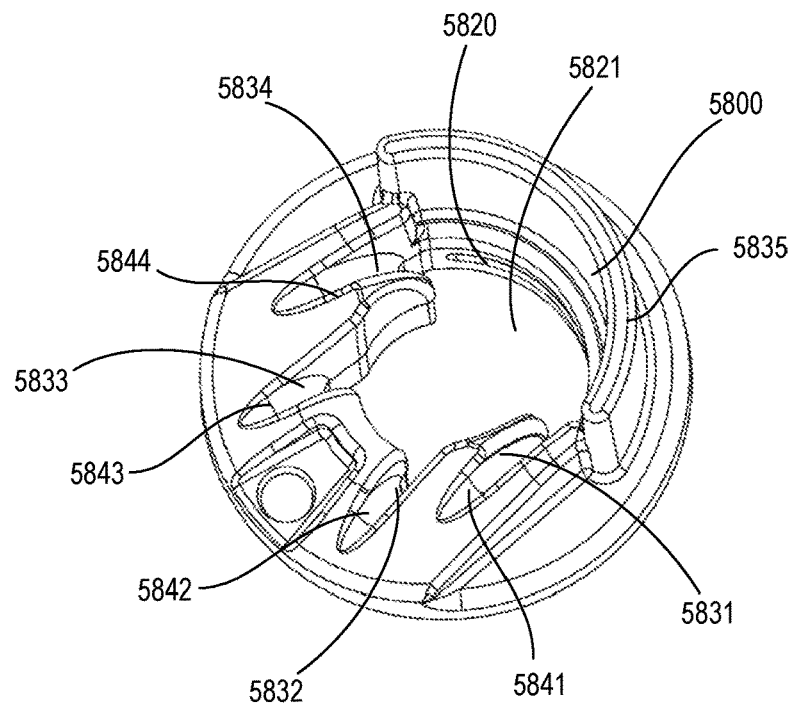
FIG. 19 is a top perspective view of a cable guide of the transmission shown in FIG. 18.
Figure 20:
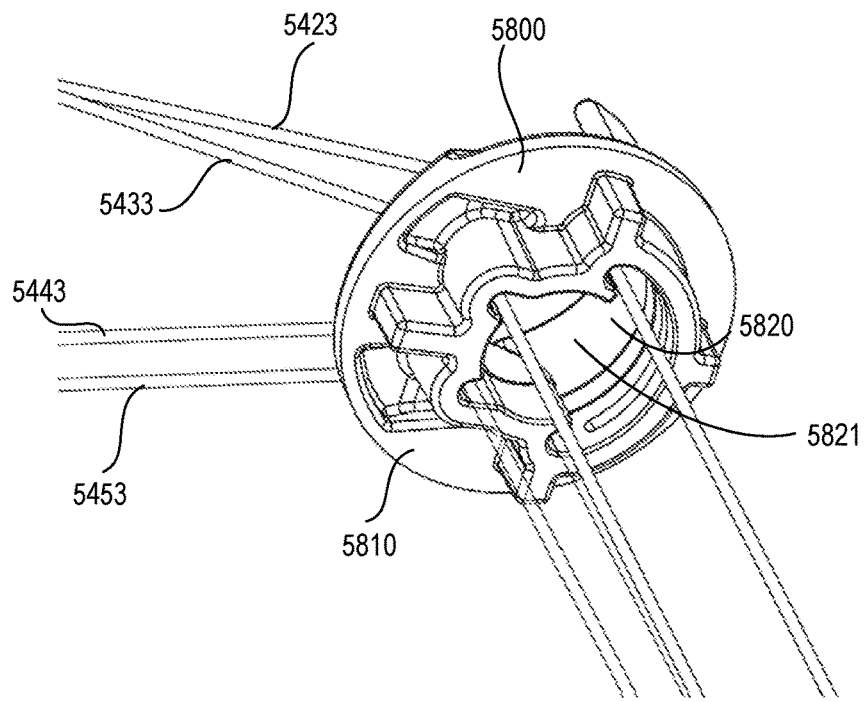
FIG. 20 is a bottom perspective view of the cable guide and the cables of the transmission shown in FIG. 18.

Although the transmission 4700 is shown and described as including capstan assemblies, in other embodiments, a transmission or an instrument can include any suitable number of capstan assemblies or cables. For example, FIGS. 18-20 are various views of a transmission 5700, according to an embodiment. The transmission 5700 can be used in any suitable instrument. The instrument, the transmission 5700, or any of the components therein are optionally parts of a surgical assembly that performs minimally invasive surgical procedures, and which can include a manipulator unit, a series of kinematic linkages, a series of cannulas, or the like. The instrument (and any of the instruments described herein) can be used in any suitable surgical system, such as the MIRS system 1000 shown and described above.

Referring to FIG. 18, the instrument includes a first cable pair 5420 (which functions as a tension member) and a second cable pair 5440 (which functions as a tension member). The first cable pair 5420 includes a cable portion 5423 and a cable portion 5433. A proximal end of the first cable pair 5420 is wrapped about the first capstan assembly 5710, as described below. A distal end of the first cable pair 5420 is coupled to and actuates a wrist or an end effector (not shown). The second cable pair 5440 includes a cable portion 5443 and a cable portion 5453. A proximal end of the second cable pair 5440 is wrapped about the second capstan assembly 5720, as described below. A distal end of the second cable pair 5440 is coupled to and actuates a wrist or an end effector (not shown). The instrument 5400 is configured such that movement of the cable pairs can produce rotation of a wrist assembly (i.e., pitch rotation), yaw rotation of an end effector, grip rotation of the tool members of the end effector about the yaw axis, or any combination of these movements.

The transmission 5700 includes a chassis 5760, a first capstan assembly 5710, a second capstan assembly 5720, and a cable guide 5800. The chassis 5760 (which functions as a housing) provides the structural support for mounting and aligning the components of the transmission 5700. For example, as shown in FIG. 18, the chassis 5760 defines an opening within which the proximal end portion 5411 of the shaft 5410 is mounted, and multiple openings within which the capstan assemblies are mounted. The shaft 5410 can be any suitable elongated shaft that couples the wrist assembly (not shown) and the end effector (not shown) to the transmission 5700. Specifically, the shaft 5410 includes a proximal end portion 5411 that is coupled to the chassis 5760. The shaft 5410 defines at least one passageway through which the cable portion 5423, the cable portion 5433, the cable portion 5443, the cable portion 5453, and other components (e.g., energized electrical wires, ground wires, or the like, not shown) can be routed from the transmission 5700 towards the wrist assembly.

The first capstan assembly 5710 includes a shaft that can be motor-driven to rotate about a capstan axle. The rotating shaft includes a portion about which an end portion of the first cable 5420 is wrapped. Thus, when the first capstan assembly 5710 rotates in a first direction, the cable portion 5423 can be moved proximally (i.e., can be pulled inward or wrapped about the rotating shaft), and the cable portion 5433 can be moved distally (i.e., can be payed-out or unwrapped from the rotating shaft). The movement of the first cable pair 5420 can be reversed by changing the direction of rotation of the first capstan assembly 5710. In a similar manner, the second capstan assembly 5720 includes a shaft about which an end portion of the second cable pair 5440 is wrapped. Thus, when the second capstan assembly 5720 rotates in a first direction, the cable portion 5443 can be moved proximally (i.e., can be pulled inward or wrapped about the rotating shaft), and the cable portion 5453 can be moved distally (i.e., can be payed-out or unwrapped from the rotating shaft). The movement of the second cable pair 5440 can be reversed by changing the direction of rotation of the second capstan assembly 5720. Referring to FIG. 18, the arrangement of the capstan assemblies and the cable guide 5800 defines a cable path for each of the cables. Through these cable paths, the cables are routed from their respective capstan assembly into the shaft 5410.

The cable guide 5800 includes a stiffening rib 5835 and is coupled to the chassis 5760. The cable guide 5800 can be coupled to the chassis 5760 by any suitable mechanism (e.g., adhesive, heat weld, or the like). The stiffening rib 5835 can stiffen the overall structure of the cable guide 5800, thereby limiting the likelihood that the cable guide 5800 will detach from (or rotate relative to) the chassis 5760. The cable guide 5800 includes an inner surface 5820 that defines a shaft opening 5821. The shaft opening 5821 opens into the passageway of the shaft 5410. Moreover, although shown as being noncircular, the shaft opening 5821 can have any suitable shape (e.g., circular, oblong, or elliptical).

The cable guide 5800 includes a first guide groove 5831, a second guide groove 5832, a third guide groove 5833, and a fourth guide groove 5834. The first cable portion 5423 is routed within the first guide groove 5831, through the shaft opening 5821, and towards the shaft passageway. The first guide groove 5831 is defined by a first guide surface 5841 and defines a first guide center line (not identified). Like the first guide surface 4841 described above, the first guide surface 5841 includes a first bend portion transitioning from the first guide groove 5831 into the shaft opening 5821. The second cable portion 5433 is routed within the second guide groove 5832, through the shaft opening 5821, and towards the shaft passageway. The second guide groove 5832 is defined by a second guide surface 5842 and defines a second guide center line (not identified). Like the second guide surface 4842 described above, the second guide surface 5842 includes a second bend portion transitioning from the second guide groove 5832 into the shaft opening 5821. The third cable portion 5443 is routed within the third guide groove 5833, through the shaft opening 5821, and towards the shaft passageway. The third guide groove 5833 is defined by a third guide surface 5843 and defines a third guide center line (not identified). Like the third guide surface 4843 described above, the third guide surface 5843 includes a third bend portion transitioning from the third guide groove 5833 into the shaft opening 5821. The fourth cable portion 5453 is routed within the fourth guide groove 5834, through the shaft opening 5821, and towards the shaft passageway. The fourth guide groove 5834 is defined by a fourth guide surface 5844 and defines a fourth guide center line (not identified). Like the fourth guide surface 4844 described above, the fourth guide surface 5844 includes a fourth bend portion transitioning from the fourth guide groove 5834 into the shaft opening 5821.

As shown in FIG. 19, the first guide groove 5831, the second guide groove 5832, the third guide groove 5833, and the fourth guide groove 5834 are splayed outward from the shaft opening 5821. Similarly stated, the guide grooves are spread out apart from the shaft opening 5821. Although not identified in FIG. 19, the guide grooves can define any suitable splay angle between them (similar to the splay angle Θ described above with reference to the cable guide 2800). For example, the splay angle between adjacent guide grooves can be, for example, between 5 degrees and 60 degrees, between 10 degrees and 45 degrees, or between 15 degrees and 30 degrees. Additionally, the bend axes can be nonparallel to any of the other bend axes. For example, the first bend axis is nonparallel to the second bend axis, the third bend axis, and the fourth bend axis. This arrangement allows the guide grooves to be splayed outward from the shaft opening 5821, as described above. All four of the bend axes, however, need not be nonparallel to each of the other bend axes. For example, in some embodiments, the second bend axis and the third bend axis can be parallel.

Figure 21:
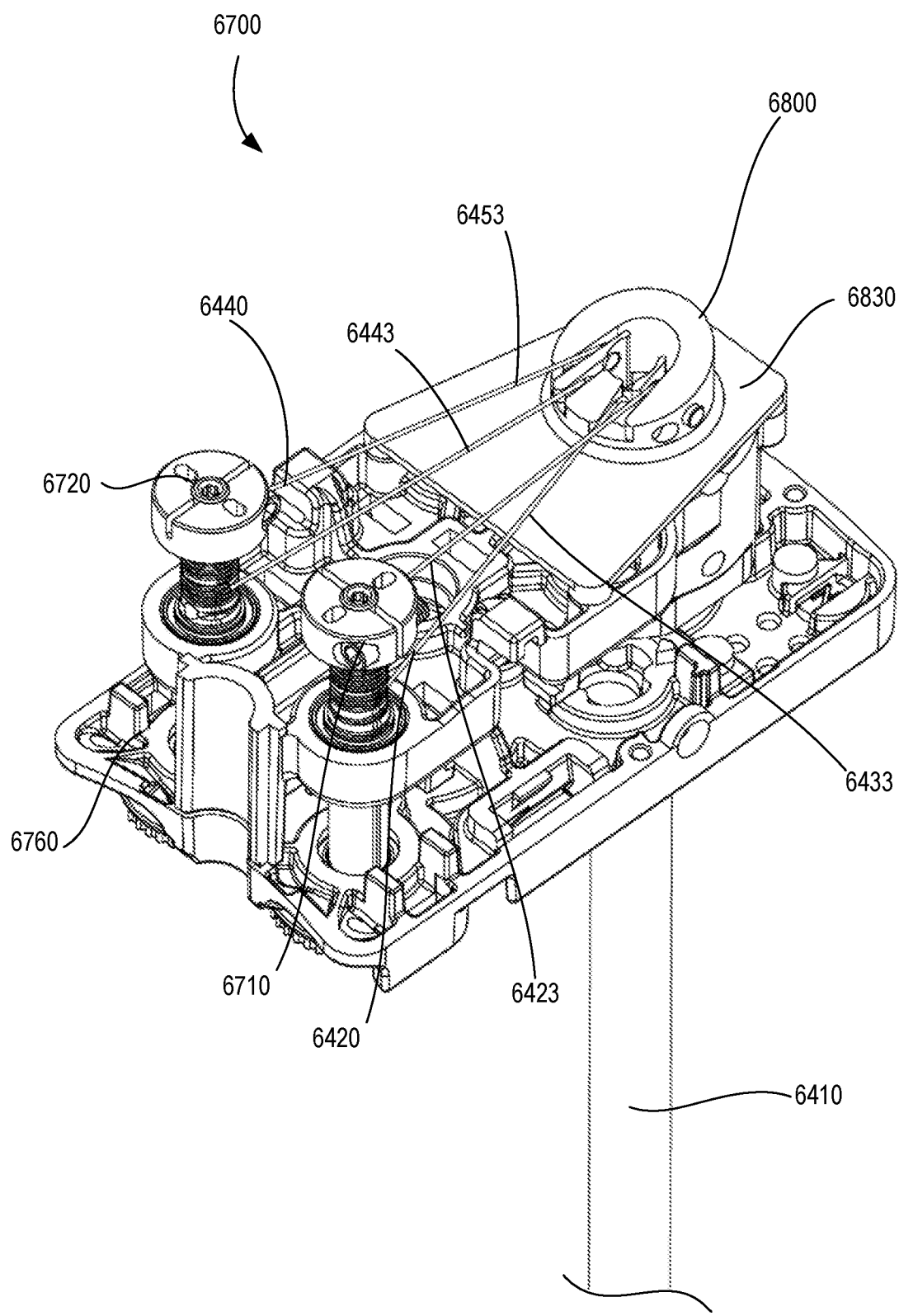
FIG. 21 is a perspective view of a transmission of an instrument, according to an embodiment.
Figure 22:
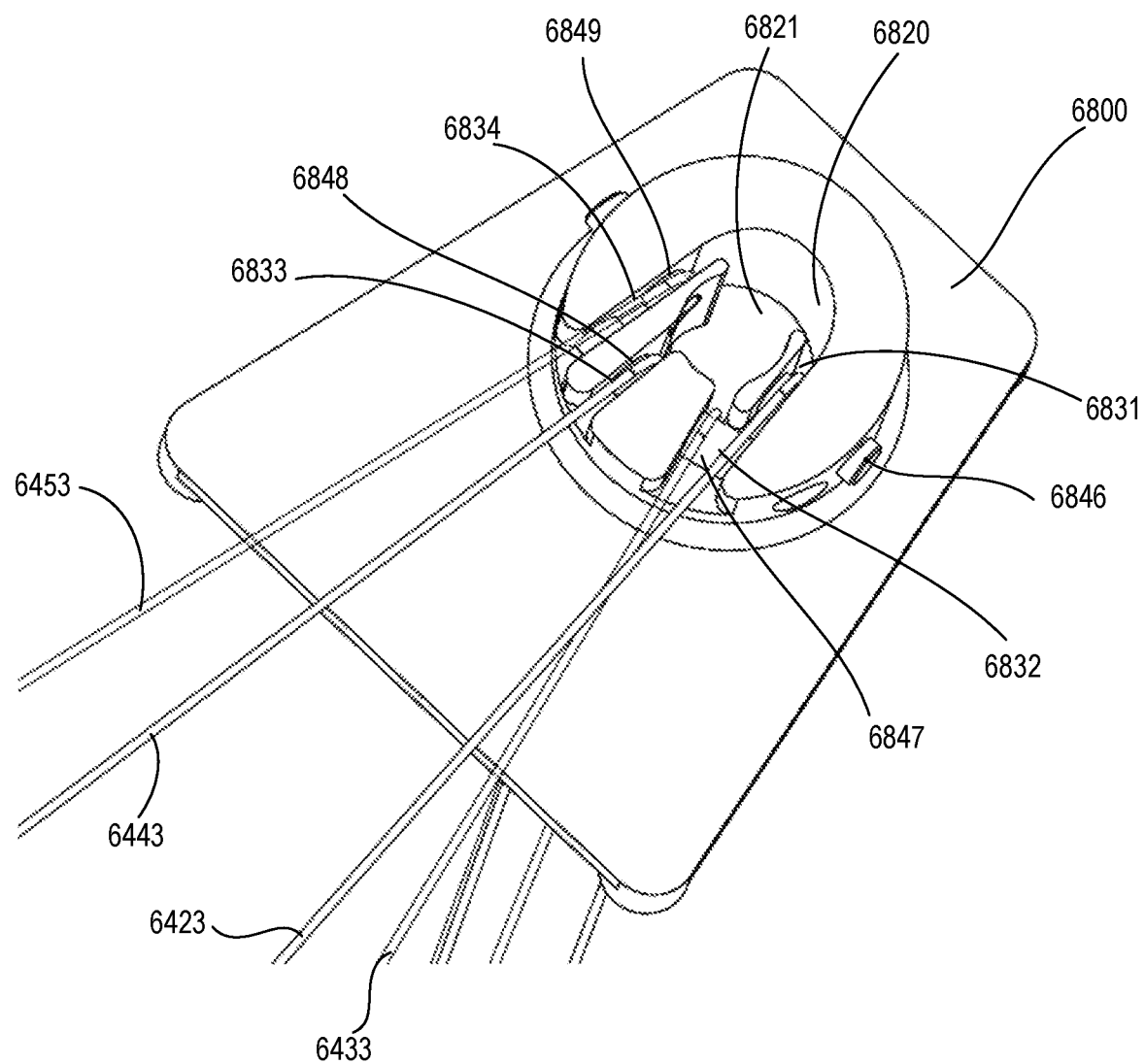
FIG. 22 is a top perspective view of a cable guide of the transmission shown in FIG. 21.
Figure 23:
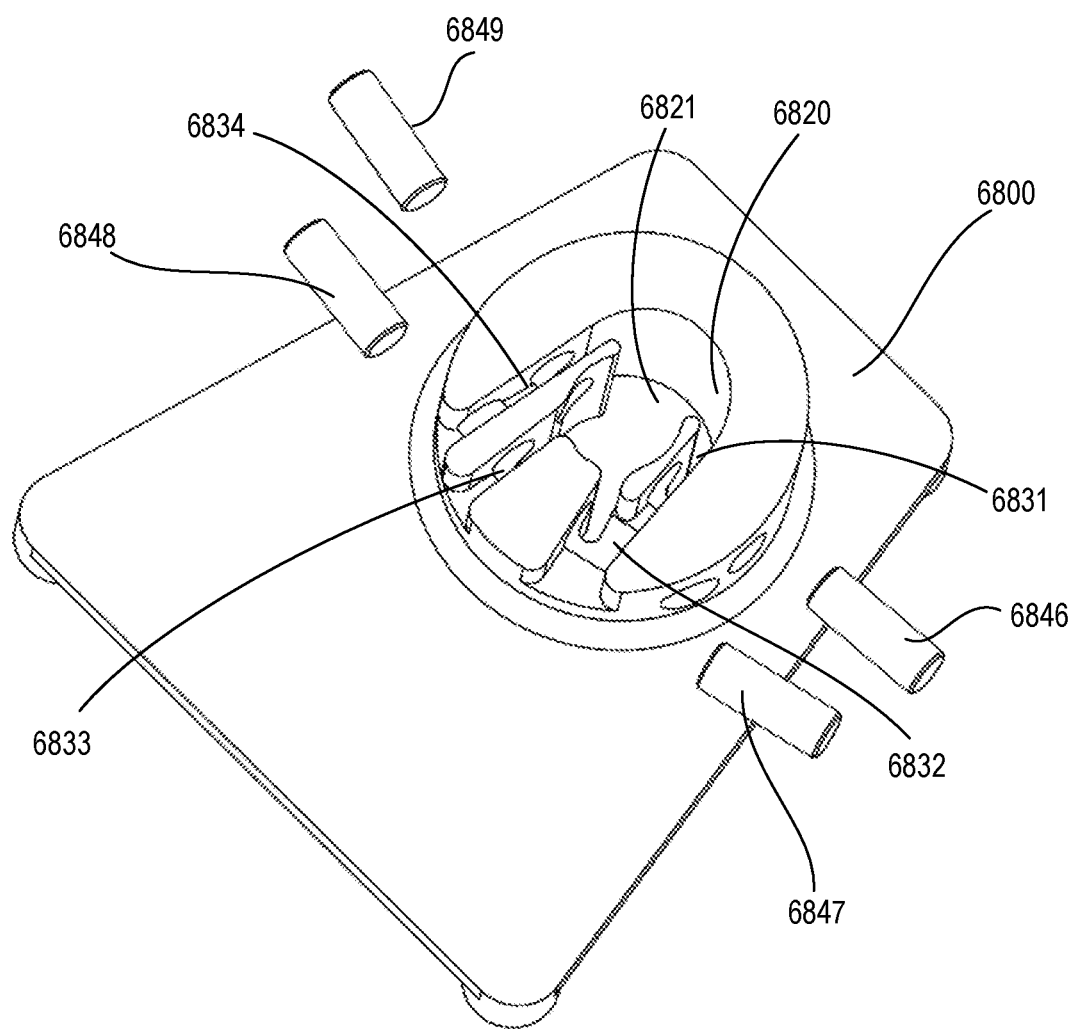
FIG. 23 is a perspective exploded view of the cable guide of the transmission shown in FIG. 21.

In some embodiments, any of the cable guides described herein can be constructed from separate components that are assembled to form the cable guide. For example, FIGS. 21-23 are various views of a transmission 6700, according to an embodiment. The transmission 6700 can be used in any suitable instrument and in any suitable surgical system, such as the MIRS system 1000 shown and described above. The instrument includes a first cable pair 6420 (which functions as a tension member) and a second cable pair 6440 (which functions as a tension member). The first cable pair 6420 includes a cable portion 6423 and a cable portion 6433. A proximal end of the first cable pair 6420 is wrapped about the first capstan assembly 6710, as described below. A distal end of the first cable pair 6420 is coupled to and actuates a wrist or an end effector (not shown). The second cable pair 6440 includes a cable portion 6443 and a cable portion 6453. A proximal end of the second cable pair 6440 is wrapped about the second capstan assembly 6720, as described below. A distal end of the second cable pair 6440 is coupled to and actuates a wrist or an end effector (not shown). The instrument 6400 is configured such that movement of the cable pairs can produce rotation of a wrist assembly (i.e., pitch rotation), yaw rotation of an end effector, grip rotation of the tool members of the end effector about the yaw axis, or any combination of these movements.

The transmission 6700 includes a chassis 6760, a first capstan assembly 6710, a second capstan assembly 6720, and a cable guide 6800. The chassis 6760 (which functions as a housing) provides the structural support for mounting and aligning the components of the transmission 6700. For example, as shown in FIG. 21, the chassis 6760 is coupled to the proximal end portion of the shaft 6410. The shaft 6410 can be any suitable elongated shaft that couples the wrist assembly (not shown) and the end effector (not shown) to the transmission 6700. The shaft 6410 defines at least one passageway through which the cable portion 6423, the cable portion 6433, the cable portion 6443, the cable portion 6453, and other components (e.g., energized electrical wires, ground wires, or the like, not shown) can be routed from the transmission 6700 towards the wrist assembly.

The first capstan assembly 6710 includes a shaft that can be motor-driven to rotate about a capstan axle. The rotating shaft includes a portion about which an end portion of the first cable 6420 is wrapped. Thus, when the first capstan assembly 6710 rotates in a first direction, the cable portion 6423 can be moved proximally (i.e., can be pulled inward or wrapped about the rotating shaft), and the cable portion 6433 can be moved distally (i.e., can be payed-out or unwrapped from the rotating shaft). The movement of the first cable pair 6420 can be reversed by changing the direction of rotation of the first capstan assembly 6710. In a similar manner, the second capstan assembly 6720 includes a shaft about which an end portion of the second cable pair 6440 is wrapped. Thus, when the second capstan assembly 6720 rotates in a first direction, the cable portion 6443 can be moved proximally (i.e., can be pulled inward or wrapped about the rotating shaft), and the cable portion 6453 can be moved distally (i.e., can be payed-out or unwrapped from the rotating shaft). The movement of the second cable pair 6440 can be reversed by changing the direction of rotation of the second capstan assembly 6720. Referring to FIG. 21, the arrangement of the capstan assemblies and the cable guide 6800 defines a cable path for each of the cables. Through these cable paths, the cables are routed from their respective capstan assembly into the shaft 6410.

The cable guide 6800 includes a top portion 6830 and is coupled to the chassis 6760. The cable guide 6800 can be coupled to the chassis 6760 by any suitable mechanism (e.g., adhesive, heat weld, or the like). The cable guide 6800 includes an inner surface 6820 that defines a shaft opening 6821. The shaft opening 6821 opens into the passageway of the shaft 6410. Moreover, although shown as being noncircular, the shaft opening 6821 can have any suitable shape (e.g., circular, oblong, or elliptical).

The cable guide 6800 includes a first guide groove 6831, a second guide groove 6832, a third guide groove 6833, and a fourth guide groove 6834. The first cable portion 6423 is routed within the first guide groove 6831, through the shaft opening 6821, and towards the shaft passageway. The first guide groove 6831 is defined by a first guide surface and a first pin 6846. The first pin 6846 is pressed into the top portion 6830 and provides a first bend portion transitioning from the first guide groove 6831 into the shaft opening 6821. The second cable portion 6433 is routed within the second guide groove 6832, through the shaft opening 6821, and towards the shaft passageway. The second guide groove 6832 is defined by a second guide surface and a second pin 6847. The second pin 6847 is pressed into the top portion 6830 and provides a second bend portion transitioning from the second guide groove 6832 into the shaft opening 6821. The third cable portion 6443 is routed within the third guide groove 6833, through the shaft opening 6821, and towards the shaft passageway. The third guide groove 6833 is defined by a third guide surface and a third pin 6848. The third pin 6848 is pressed into the top portion 6830 and provides a third bend portion transitioning from the third guide groove 6833 into the shaft opening 6821. The fourth cable portion 6453 is routed within the fourth guide groove 6834, through the shaft opening 6821, and towards the shaft passageway. The fourth guide groove 6834 is defined by a fourth guide surface and a fourth pin 6849. The fourth pin 6849 is pressed into the top portion 6830 and provides a fourth bend portion transitioning from the fourth guide groove 6834 into the shaft opening 6821.

As shown in FIG. 22, the first guide groove 6831, the second guide groove 6832, the third guide groove 6833, and the fourth guide groove 6834 are splayed outward from the shaft opening 6821. Similarly stated, the guide grooves are spread out apart from the shaft opening 6821. Although not identified in FIG. 22, the guide grooves can define any suitable splay angle between them (similar to the splay angle Θ described above with reference to the cable guide 2800). For example, the splay angle between adjacent guide grooves can be, for example, between 5 degrees and 60 degrees, between 10 degrees and 45 degrees, or between 15 degrees and 30 degrees. Additionally, the bend axes can be nonparallel to any of the other bend axes. For example, the first bend axis is nonparallel to the second bend axis, the third bend axis, and the fourth bend axis. This arrangement allows the guide grooves to be splayed outward from the shaft opening 6821, as described above. All four of the bend axes, however, need not be nonparallel to each of the other bend axes. For example, in some embodiments, the second bend axis and the third bend axis can be parallel.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, although the guide grooves are shown and described herein as being linear, in other embodiments any of the guide grooves described herein can be curved (i.e., can have a curved guide center line).

Any of the tension members described herein can be formed as a cable made of Tungsten or stainless steel to provide sufficient strength, bendability and durability. In some embodiments, cables can be constructed from multiple braids of fine wire, to provide strength and resiliency. In some embodiments, cables can be made from 150 to 350 braids of 0.0007 inch to 0.001 inch (0.01778 mm to 0.0254 mm) diameter tungsten wire providing cables with outer diameters of 0.014 inches to 0.018 inches (0.3556 mm to 0.4572 mm). Moreover, although shown and described as guiding cables, any of the guide structures described herein can be adapted for use with any suitable tension member. For example, in some embodiments, the transmission 2700 (and any of the transmissions or instruments described herein) can include a tension member having any suitable cross-sectional shape. For example, in some embodiments, the transmission 2700 (and any of the transmissions or instruments described herein) can include a tension band, of the types shown and described in U.S. Patent Application No. 62/598,620 (filed Dec. 14, 2017), entitled "Medical Tools Having Tension Bands," which is incorporated herein by reference in its entirety.

In some embodiments, any of the guide surfaces described herein can be coated, treated or otherwise produced to have a low-friction surface. For example, in some embodiments, any of the guide surfaces can be characterized by a coefficient of friction of less than 0.1. In some embodiments, any of the guide surfaces can be coated with a friction-reducing composition.

In some embodiments, any of the guide surfaces described herein can be constructed from a low-friction material that reduces the frictional losses between the cables and the cable guide. For example, in some embodiments, any of the cable guides described herein can be monolithically constructed from a low friction material. Such materials can include, for example, polyether ether ketone (PEEK) filled with at least one of a glass material or polytetrafluoroethylene (PTFE). In some embodiments, any of the cable guides described herein can be monolithically constructed from any suitable material (e.g., polymer, metal, composite) and can include a friction-reducing coating on the guide surfaces. In yet other embodiments, any of the cable guides described herein can be constructed from separate components that are assembled to form the cable guide.

Although the cable guide 4800 is shown as being constructed separately from and attached to the upper housing 4765, in other embodiments, the cable guide and the upper housing can be monolithically constructed.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

For example, although the first guide path 2831 is described above as having a bend angle $\beta$ (i.e., between the first guide center line $CL_1$ and the opening center line $CL_{OP}$) of greater than 45 degrees, greater than 60 degrees, or greater than 75 degrees, in other embodiments, any of the guide paths described here can have a bend angle like that described for the first guide path 2831. For example, any of the guide paths of the cable guide 4800 can have a bend angle of greater than 45 degrees, greater than 60 degrees, or greater than 75 degrees.

What is claimed is:

1. A medical device, comprising:
an instrument shaft, a housing coupled to the instrument shaft, a cable guide, a first cable, and a second cable;
the instrument shaft comprising a shaft passageway and a shaft center line;
the cable guide comprising a first guide surface, a second guide surface, one or more protrusions, and an opening;
the one or more protrusions being engaged with the housing to align the opening of the cable guide with the shaft passageway;
the first guide surface comprising a first bend portion transitioning into the opening, and the first bend portion being at a first position with reference to the shaft center line;
the second guide surface comprising a second bend portion transitioning into the opening, the second bend portion being at a second position with reference to the shaft center line, and the second position being different than the first position;
the first cable being routed along the first guide surface, around the first bend portion, through the opening, and into the shaft passageway; and
the second cable being routed along the second guide surface, around the second bend portion, through the opening, and into the shaft passageway.

2. The medical device of claim 1, wherein:
the cable guide, the first guide surface, and the second guide surface are monolithically constructed.

3. The medical device of claim 1, wherein:
the first guide surface and the first bend portion are in a fixed position relative to the cable guide.

4. The medical device of claim 1, wherein:
the first cable comprises a central portion routed within the shaft passageway;
the second cable comprises a central portion routed within the shaft passageway; and
the first position of the first bend portion and the second position of the second bend portion are such that the central portion of the first cable and the central portion of the second cable are each spaced apart from the shaft center line.

5. The medical device of claim 4, wherein:
the central portion of the first cable is at a first circumferential position on a circumference defined around the shaft center line;
the central portion of the second cable is at a second circumferential position on the circumference; and
the second circumferential position is different from the first circumferential position.

6. The medical device of claim 4, wherein:
the central portion of the first cable is at a first radial position with reference to the shaft center line;
the central portion of the second cable is at a second radial position with reference to the shaft center line; and
the second radial position is different from the first radial position.

7. The medical device of claim 1, wherein:
the first bend portion is at a first height above the opening;
the second bend portion is at a second height above the opening; and
the second height is different from the first height.

8. The medical device of claim 1, wherein:
a first guide groove is defined in the first guide surface;
a second guide groove is defined in the second guide surface;
the first cable is routed within the first guide groove; and
the second cable is routed within the second guide groove.

9. The medical device of claim 8, wherein:
the first guide groove defines a first groove center line; and
the second guide groove defines a second groove center line nonparallel to the first groove center line.

10. The medical device of claim 1, wherein:
the first bend portion defines a first bend angle of more than 60 degrees.

11. The medical device of claim 1, further comprising:
a capstan mounted within the housing,
wherein the first cable comprises a proximal end coupled to the capstan.

12. The medical device of claim 11, wherein:
the first cable extends from the cable guide to the capstan in a straight line.

13. A medical device, comprising:
an instrument shaft comprising a proximal end, a distal end, and a shaft center line extending between the proximal end and the distal end;
a housing coupled to the instrument shaft;
a first cable;
a second cable; and
means for guiding the first cable and the second cable into the proximal end of the instrument shaft,
the means for guiding comprising a first fixed groove for bending the first cable at a first position relative to the shaft center line,
the means for guiding comprising a second fixed groove for bending the second cable at a second position relative to the shaft center line different from the first position, and
the first fixed groove defines a bend angle of more than 60 degrees.

14. The medical device of claim 13, wherein:
the means for guiding is a monolithic piece.

15. The medical device of claim 13, wherein:
the first position is a first circumferential position with reference to the shaft center line; and
the second position is a second circumferential position with reference to the shaft center line.

16. The medical device of claim 13, wherein:
the first fixed groove is nonparallel to the second fixed groove.

17. A medical device, comprising:
an instrument shaft, a cable guide, a first cable, and a second cable;
the instrument shaft comprising a shaft passageway and a shaft center line;
the cable guide comprising a first guide surface, a second guide surface, and an opening;
the first guide surface comprising a first bend portion transitioning into the opening, the first bend portion being at a first position with reference to the shaft center line, and the first bend portion defining a first bend angle of more than 60 degrees;
the second guide surface comprising a second bend portion transitioning into the opening, the second bend portion being at a second position with reference to the shaft center line, and the second position being different than the first position;
the first cable being routed along the first guide surface, around the first bend portion, through the opening, and into the shaft passageway; and
the second cable being routed along the second guide surface, around the second bend portion, through the opening, and into the shaft passageway.

18. The medical device of claim 17, wherein:
the cable guide, the first guide surface, and the second guide surface are monolithically constructed.

19. The medical device of claim 18, wherein:
a first guide groove is defined in the first guide surface;
a second guide groove is defined in the second guide surface;
the first cable is routed within the first guide groove; and
the second cable is routed within the second guide groove.

20. The medical device of claim 17, wherein:
the first cable comprises a central portion routed within the shaft passageway;
the second cable comprises a central portion routed within the shaft passageway; and
the first position of the first bend portion and the second position of the second bend portion are such that the central portion of the first cable and the central portion of the second cable are each spaced apart from the shaft center line.

* * * * *